(12) United States Patent  
Imura et al.

(10) Patent No.: US 7,355,712 B2  
(45) Date of Patent: Apr. 8, 2008

(54) APPARATUS FOR MEASURING GONIOMETRIC REFLECTION PROPERTY OF SAMPLE

(75) Inventors: Kenji Imura, Toyohashi (JP); Kazuya Kiyoi, Tondabayashi (JP); Katsutoshi Tsurutani, Osaka (JP)

(73) Assignee: Konica Minolta Sensing, Inc., Osaka (JP)

( * ) Notice: Subject to any disclaimer, the term of this patent is extended or adjusted under 35 U.S.C. 154(b) by 86 days.

(21) Appl. No.: 11/472,981

(22) Filed: Jun. 22, 2006

(65) Prior Publication Data

US 2006/0290936 A1 Dec. 28, 2006

(30) Foreign Application Priority Data

Jun. 24, 2005 (JP) ............................. 2005-185387

(51) Int. Cl.
*G01N 21/55* (2006.01)
(52) U.S. Cl. ....................... 356/445; 356/446
(58) Field of Classification Search ......... 356/445–448
See application file for complete search history.

(56) References Cited

U.S. PATENT DOCUMENTS 6,707,553 B1  3/2004  Imura

2003/0133121 A1 *  7/2003  Davis et al. ............... 356/445

OTHER PUBLICATIONS

Fig. 14 of present application filed Jun. 22, 2006 entitled "Apparatus for Measuring Goniometric Reflection Property of Sample,".
Fig. 15 of present application filed Jun. 22, 2006 entitled "Apparatus for Measuring Goniometric Reflection Property of Sample,".

* cited by examiner

*Primary Examiner*—Tarifur Chowdhury
*Assistant Examiner*—Tara S Pajoohi
(74) *Attorney, Agent, or Firm*—Brinks Hofer Gilson & Lione

(57) ABSTRACT

An apparatus for measuring a goniometric reflection property of a sample has: one or more illuminators; a toroidal mirror which is rotationally symmetrical around a center axis effectively contacting with a surface of the sample; a light receiver having an incident aperture on the center axis; a rotating optics which rotates around a rotation axis which effectively coincides with the center axis; and a controller for controlling operations of the illuminators, the light receiver, and the rotating optics, wherein the toroidal mirror reflects light fluxes emitted from the surface of the sample illuminated by the one or more illuminators in emitting directions perpendicular to the center axis and directs each of the light fluxes to the center axis, and wherein the rotating optics specifies one of the light fluxes reflected by the toroidal mirror and directs the specified light flux to the incident aperture of the light receiver.

12 Claims, 14 Drawing Sheets

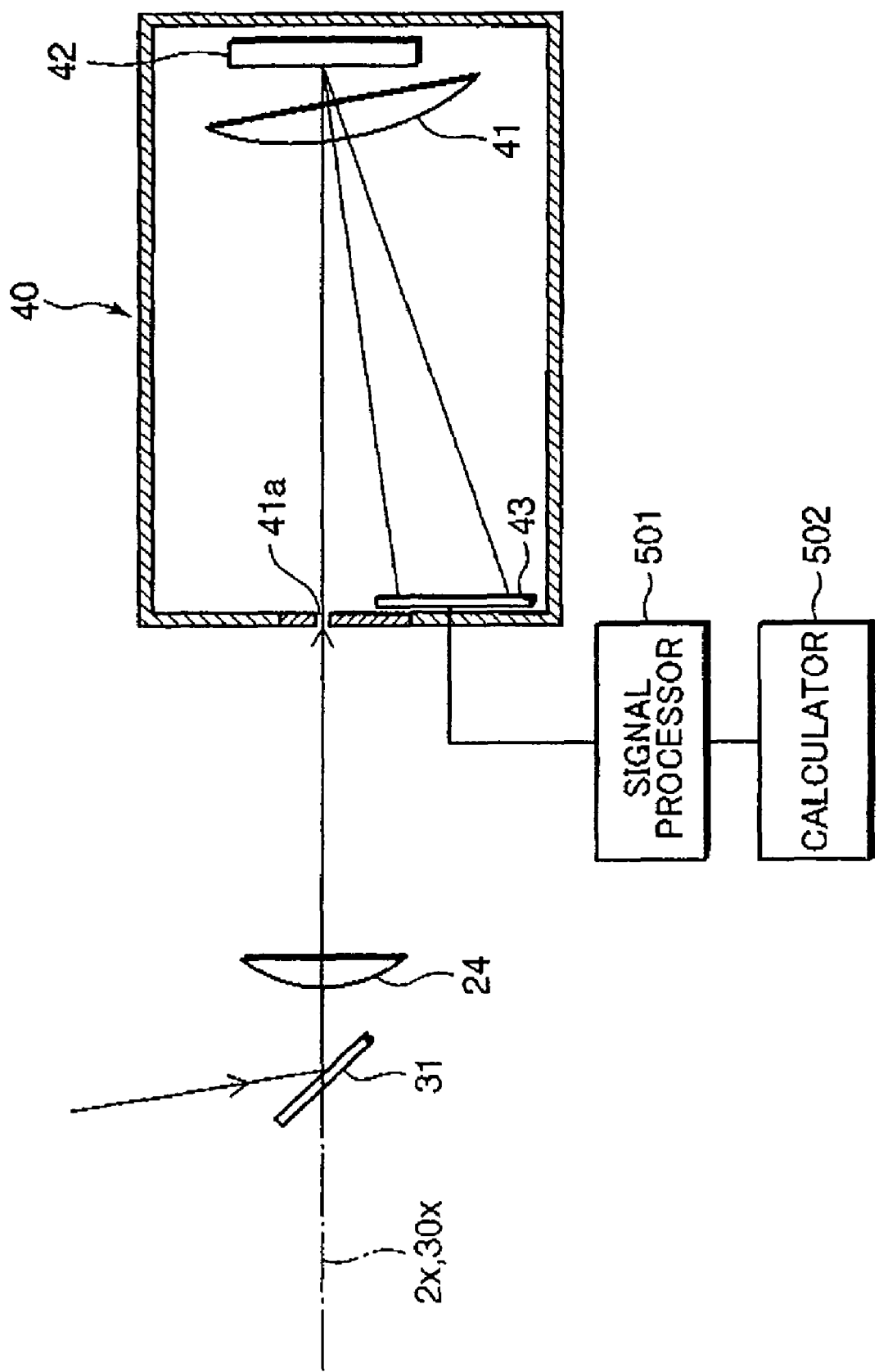

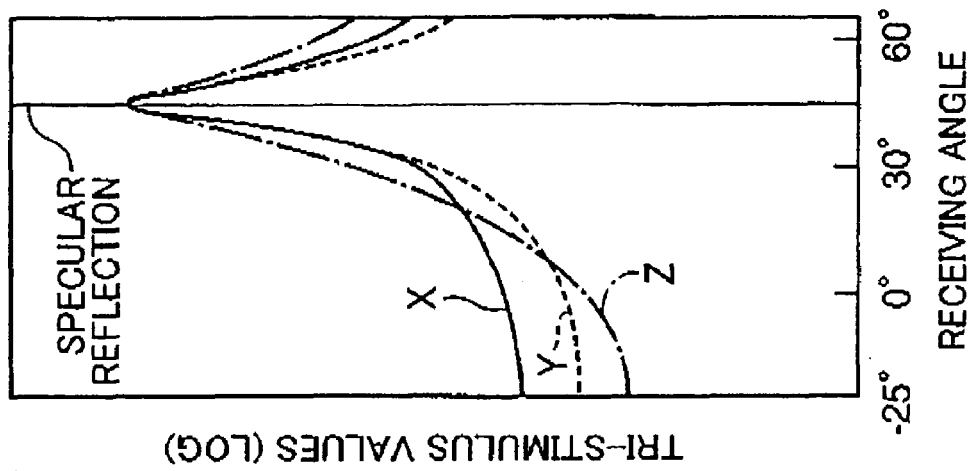
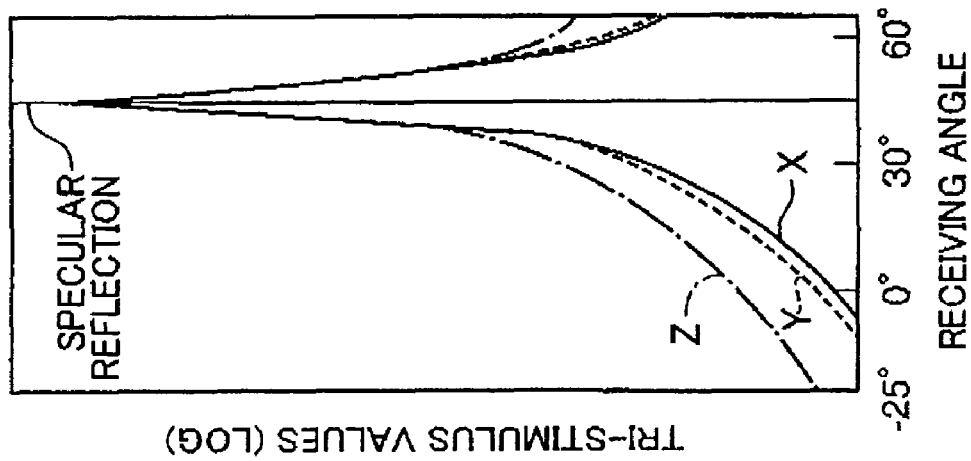
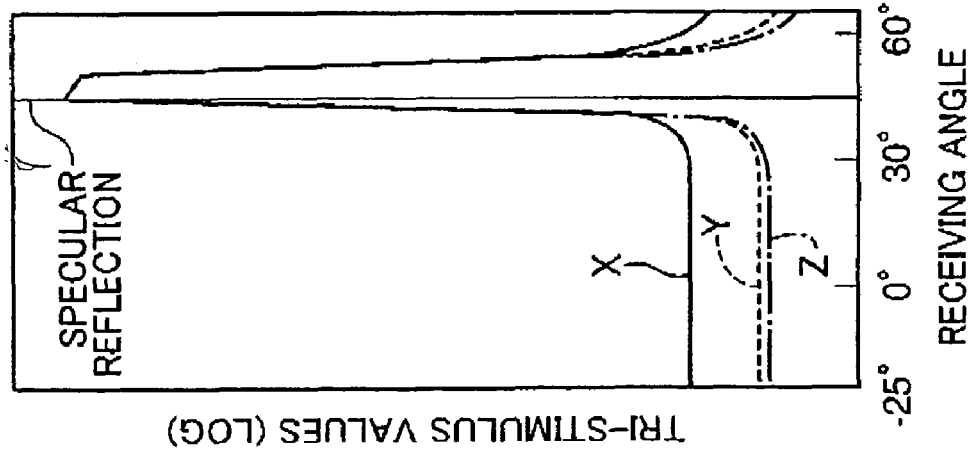

APPARATUS FOR MEASURING GONIOMETRIC REFLECTION PROPERTY OF SAMPLE

This application is based on Japanese Patent Application No. 2005-185387 filed on Jun. 24, 2005, the contents of which are hereby incorporated by reference.

BACKGROUND OF THE INVENTION

1. Field of the Invention

The present invention relates to a goniometric spectrophotometer for measuring, in different illuminating or viewing directions, a special effect paint such as a metallic paint or a pearlescent paint appearing differently depending on an illuminating direction or a viewing direction.

2. Description of the Related Art

In a metallic paint or a pearlescent paint used for an exterior coating of automobile or the like, aluminum flakes or mica flakes called a special effect pigment is contained in a paint film, which provides a metallic effect or a pearlescent effect. Such an effect is provided because contribution of the special effect pigment to reflection characteristics is varied depending on an illuminating direction and a viewing direction. For color evaluation or colorimetric measurement of the metallic paint or the pearlescent paint, the following measuring apparatuses are used.

(1) a multi-angle spectrophotometer provided with a multi-angle geometry of illuminating from multiple directions and receiving from a single direction (multi angle illumination—directional receiving), or illuminating from a single direction and receiving from multiple directions (directional illumination—multi angle receiving); and (2) a goniometric spectrophotometer capable of arbitrarily setting an illuminating direction or a receiving direction.

FIG. 14 is a schematic illustration showing an optical system S11 of a conventional multi-angle spectrophotometer of multi-angle illumination-directional receiving geometry. The optical system S11 has three illuminators 110, 120, and 130 arranged at three different angular positions with respect to a surface 1 of a sample, and a light receiver 140 arranged at a specified angular position. The illuminators 110, 120, and 130 are respectively set at 20 degrees, 0 degree, and –30 degrees with respect to a normal 1n to the surface 1 of the sample placed in a sample aperture (not shown), and the light receiver 140 is set at –45 degrees with respect to the normal 1n. The illuminators 110, 120, and 130 respectively include light sources 111, 121, and 131, and collimating lenses 112, 122, and 132 for collimating light fluxes emitted from the respective light sources 111, 121, and 131 into collimated light fluxes 113, 123, and 133 in the respective illuminating directions. The light receiver 140 has a spectral analyzer 141, and a collimating lens 142 for converging reflected light fluxes from the sample surface 1 to an incident aperture 141a of the spectral analyzer 141.

An operation of the multi-angle spectrophotometer provided with the optical system S11 is described. First, the light sources 111, 121, and 131 of the illuminators 110, 120, and 130 are sequentially turned on by an unillustrated control calculating unit. Light fluxes emitted from the light sources 111, 121, and 131 are respectively collimated into collimated light fluxes by the collimating lenses 112, 122, and 132, so that the collimated light fluxes from the respective illuminating directions are projected onto the sample surface 1. Then, a reflected light flux 143 from the sample surface 1 with an anormal angle of –45 degrees is converged to the incident aperture 141a of the spectral analyzer 141 by the collimating lens 142. The spectral analyzer 141 is provided with an unillustrated diffraction grating and a photo sensor array. The light flux through the incident aperture 141a is dispersed by the diffraction grating in the spectral analyzer 141 with respect to each wavelength component for calculating the spectral intensity of the dispersed light flux. Also, spectral reflectance factors of the sample surface 1 in the respective illuminating directions are calculated based on the spectral intensities of the reflected light fluxes 143 of the illumination light fluxes emitted from the illuminators 110, 120, and 130 at the different angular positions to the sample surface 1. The thus obtained spectral reflectance factors are converted into colorimetric values or the like. In this way, a color evaluation value for the sample surface 1 is acquired.

FIG. 15 is a schematic illustration of an optical system S12 of a goniometric spectrophotometer of directional illumination—gonio receiving geometry. The optical system S12 has an illuminator 150 arranged at an anormal angle of 45 degrees with respect to a normal 1n to a surface 1 of a sample placed in a sample aperture (not shown), and a light receiver 140 which is rotationally movable around an axis 1c on a measurement area of the sample surface 1 in the directions shown by the arrows 144. The light receiver 140 is loaded on an arm pivoted on the axis 1c, and is controllably moved by controlling the pivot angle of the arm by a driving means.

An operation of the goniometric spectrophotometer provided with the optical system S12 is described. First, when the light receiver 140 is moved to a position capable of receiving a reflected light flux in a certain receiving direction by an unillustrated control calculating unit, a light source 151 of the illuminator 150 is turned on. A light flux emitted from the light source 151 is collimated by a collimating lens 152 so that the collimated light flux is projected onto the sample surface 1. Then, a reflected light flux 143 from the sample surface 1 in a receiving direction depending on the position of the light receiver 140 is converged to an incident aperture 141a of a spectral analyzer 141 by a collimating lens 142 for calculating the spectral intensity of the reflected light flux 143. Then, the light receiver 140 is moved to a succeeding receiving position to calculate a spectral intensity of the reflected light flux 143 in the succeeding receiving direction in a similar manner as mentioned above. The control calculating unit calculates spectral reflectance factors of the sample surface 1 in the respective receiving directions based on the spectral intensities of the reflected light fluxes 143 from the sample surface 1 in the respective receiving directions. The thus obtained spectral reflectance factors are converted into colorimetric values or the like. In this way, a color evaluation value for the sample surface 1 is acquired.

In the goniometric spectrophotometer provided with the optical system S12, the receiving angle can be arbitrarily set with respect to the illuminating direction. Accordingly, more detailed spectral intensity information in terms of angles can be acquired, as compared with the conventional multi-angle spectrophotometer. For instance, colorimetric values of a metallic paint can be sufficiently precisely measured by the multi-angle spectrophotometer. However, the goniometric spectrophotometer capable of flexibly setting the receiving angle is advantageous in color evaluation of a pearlescent paint whose spectral reflectance is varied greatly depending on a viewing direction corresponding to a reflecting angle. Also, paints having special reflection effects have been yearly developed for an exterior coating of automobile or the like. The goniometric spectrophotometer is superior in the aspect that an optimal geometry can be established depending on reflection characteristics of the special effects paints.

As mentioned above, the goniometric spectrophotometer has flexibility in setting a geometry because it can arbitrarily set a receiving angle with respect to an illuminating direction. However, size increase and weight increase of the goniometric spectrometer is unavoidable because a mechanism for rotationally moving the light receiver 140 including the spectral analyzer 141 is indispensable. Also, it takes a considerable time to move the light receiver 140 as a whole with a necessary precision. In view of the above, it is mechanically difficult to make the size of the conventional goniometric spectrophotometer as shown in FIG. 15 more compact to such an extent that the spectrophotometer can be handled with one hand by an operator for color control of automobile bodies, for instance.

SUMMARY OF THE INVENTION

In view of the above problems residing in the prior art, it is an object of the present invention to provide a compact, lightweight, portability-oriented goniometric spectrophotometer that enables to easily and arbitrarily set a receiving angle with respect to an illuminating direction in a short period.

To accomplish the object, an apparatus of the present invention for measuring a goniometric reflection property of a sample comprises: one or more illuminators; a toroidal mirror which is rotationally symmetrical around a center axis effectively contacting with a surface of a sample; a light receiver having an incident aperture on the center axis; a rotating optics which rotates around a rotation axis which effectively coincides with the center axis; and a controller for controlling operations of the illuminators, the light receiver, and the rotating optics, wherein the toroidal mirror reflects a light flux emitted from the surface of the sample illuminated by the one or more illuminators in emitting directions perpendicular to the center axis and directs each of the light fluxes to the center axis, and wherein the rotating optics specifies one of the light fluxes reflected by the toroidal mirror and directs the specified light flux to the incident aperture of the light receiver.

These and other objects, features and advantages of the present invention will become more apparent upon reading the following detailed description along with the accompanying drawings.

BRIEF DESCRIPTION OF THE DRAWINGS

FIG. 5 is an illustration showing an example of a spectral analyzer.

FIGS. 6A to 6C are graphs showing reflection characteristics of a generally available solid paint, a metallic paint, and a pearlescent mica paint, respectively.

DETAILED DESCRIPTION OF THE PREFERRED EMBODIMENTS

In the following, embodiments of the invention are described. The terminology in the following explanation is substantially based on ASTM E2175-01 "Standard Practice for Specifying the Geometry of Multi-angle Spectrophotometer".

First Embodiment

Figure 1:
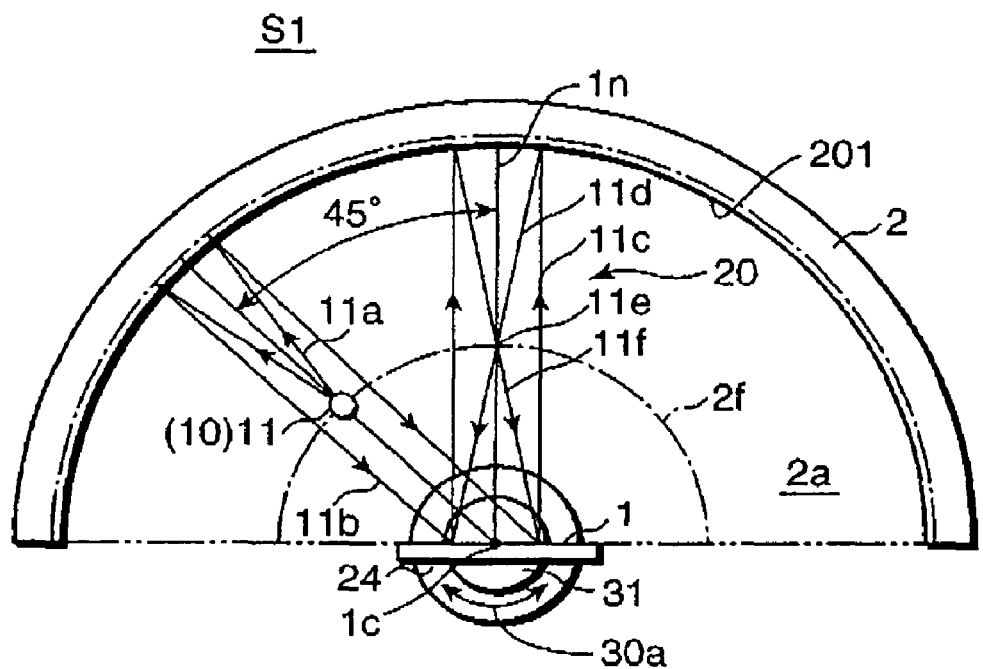
FIG. 1 is a front view showing an arrangement of a principle optical system in a goniometric spectrophotometer in accordance with a first embodiment of the invention.
Figure 2:
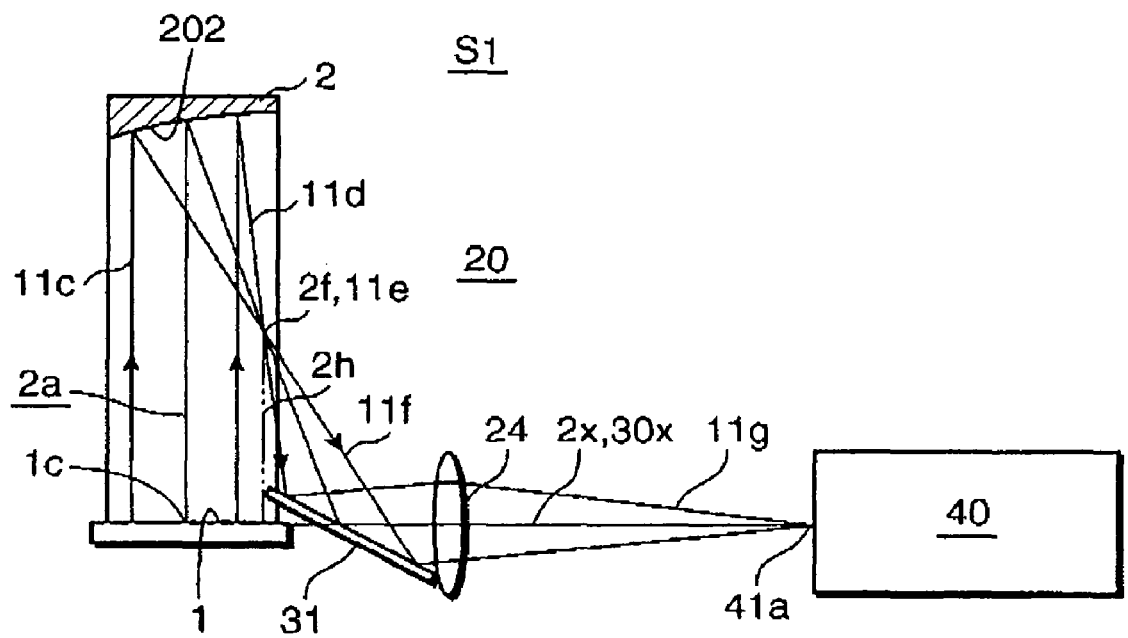
FIG. 2 is a cross-sectional side view of the optical system shown in FIG. 1 in a plane perpendicular to FIG. 1 and including a normal to a sample surface.
Figure 3:
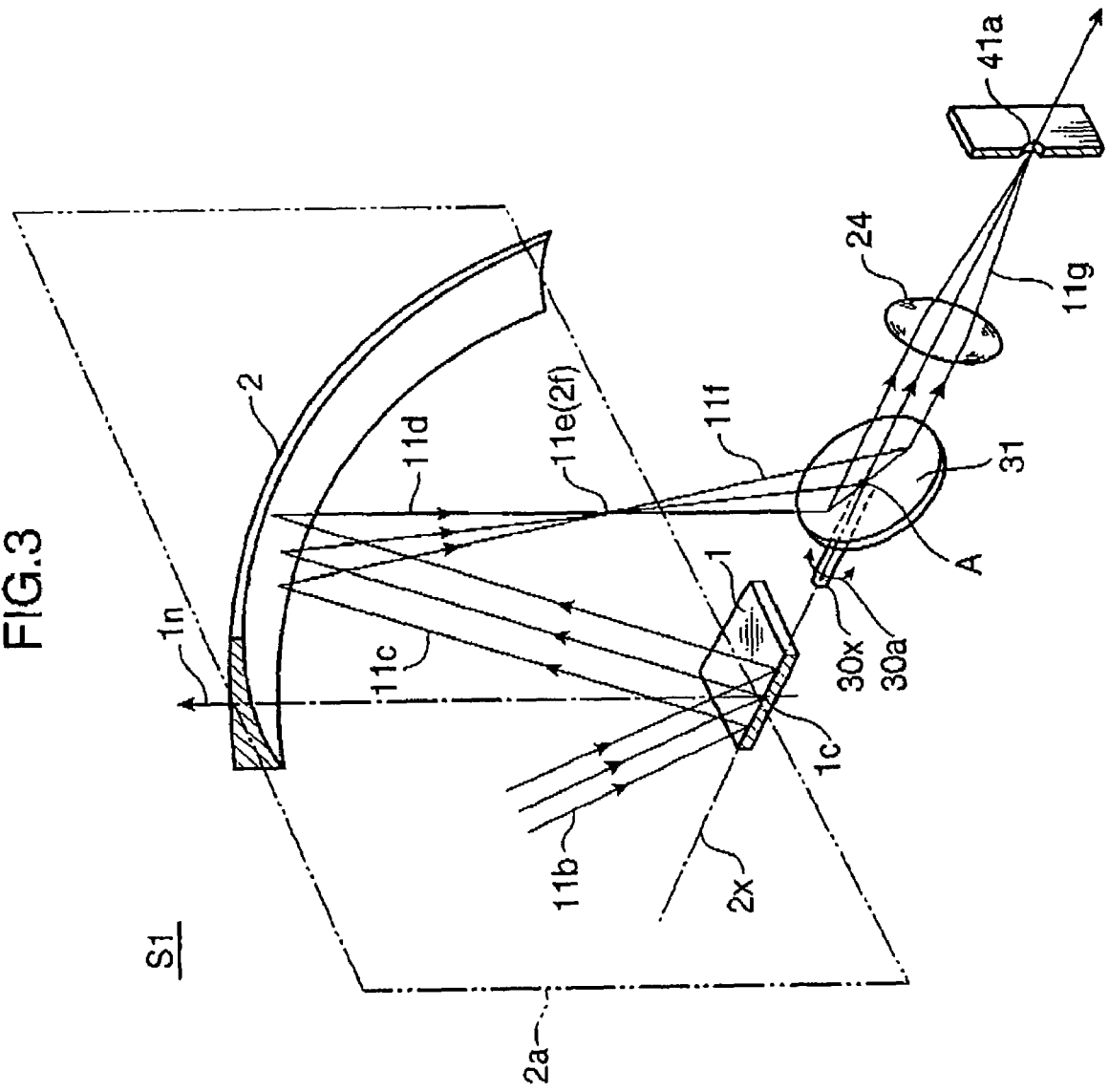
FIG. 3 is a perspective view of the principle optical system.

FIG. 1 is a front view showing an arrangement of a principle optical system S1 of a goniometric spectrophotometer i.e. an apparatus for measuring goniometric reflection characteristics of a sample according to a first embodiment. FIG. 2 is a cross-sectional side view of the optical system S1 in a plane perpendicular to FIG. 1 and including a normal 1n to a surface 1 of a sample placed in a sample aperture (not shown). FIG. 3 is a perspective view of the principle optical system. As shown in FIGS. 1 through 3, the optical system S1 includes: a toroidal mirror 2 rotationally symmetrical around a center axis 2x substantially contacting with the sample surface 1 (or the sample aperture) coated with a pearlescent paint or the like; an illumination system 10 for illuminating the sample surface 1 with an illumination light flux: a receiving optics 20 for receiving a reflected light flux from the sample surface 1; and a spectral analyzer 40 for measuring a spectral intensity of the reflected light flux received by the receiving optics 20. In the case of an apparatus for measuring goniometric reflection characteristics of a sample, a receiving optics for measuring an intensity of a reflected light flux is provided in place of the spectral analyzer 40. The receiving optics 20 includes a plane mirror 31 serving as a rotating optics, and a relay lens 24 serving as a relay optics. The relay lens 24 is a fixed optics that does not rotate.

The toroidal mirror 2 is a concave mirror having different cross sections from each other in two perpendicular planes. The toroidal mirror 2 of this embodiment is a part of a ring shaped concave mirror symmetrical around the center axis 2x contacting with the sample aperture.

Specifically, the toroidal mirror 2 has a circular cross section 201 in a plane 2a (hereinafter, referred to as "measurement plane 2a") (see FIG. 3) perpendicular to the center axis 2x and including the normal in to the sample surface 1 at a center 1c, and parabolic cross sections 202 in planes including the center axis 2x. The focus point of each of the parabolic cross sections 202 is located on a circle 2f (hereinafter, referred to as "focus point circle 2f") in the plane parallel to and apart by a predetermined distance from the measurement plane 2a centered at the center axis 2x whose radius is around half of that of the toroidal mirror 2. The axis of symmetry of each of the parabolic cross sections 202 perpendicularly crosses the center axis 2x and includes the focus point.

With the thus shaped toroidal mirror 2, reflected light fluxes from the sample surface 1 in the respective illuminating directions around the center axis 2x parallel to the measurement plane 2a perpendicular to the center axis 2x are reflected on the toroidal mirror 2. The reflected light fluxes reflected on the toroidal mirror 2 are converged at respective focus points on the focus point circle 2f of the toroidal mirror 2 corresponding to the respective illuminating directions around the center axis 2x.

Figure 14:
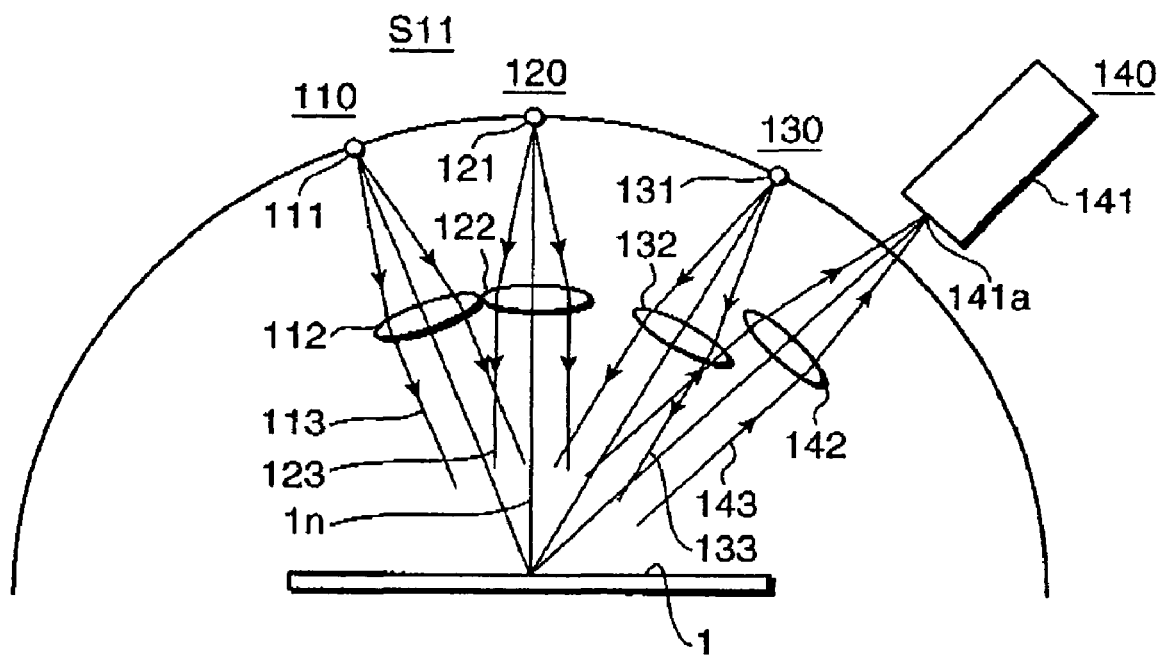
FIG. 14 is an illustration showing an optical system in a conventional multi-angle spectrophotometer of multi angle illumination—gonio receiving geometry.
Figure 15:
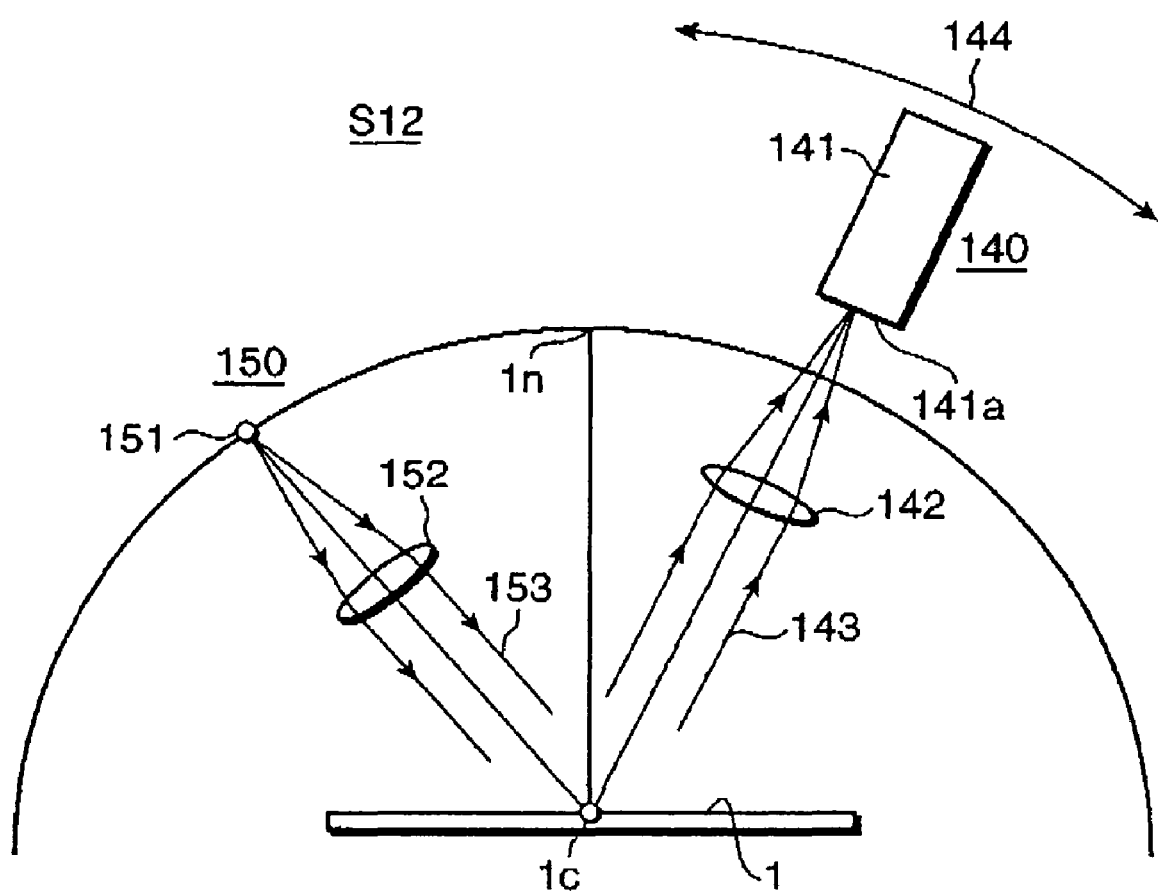
FIG. 15 is an illustration showing an optical system in a conventional goniometric spectrophotometer of directional illumination—gonio receiving geometry.

The illumination system 10 includes a light source 11 which is disposed on the focus point circle 2f of the toroidal mirror 2 with an anormal angle of 45 degrees with respect to the normal 1n. An illumination light flux emitted from the light source 11 does not directly illuminate the sample surface 1, but is projected onto the sample surface 1 after being collimated by reflection on the toroidal mirror 2, as shown in FIG. 1. The illumination system 10 of the above-mentioned arrangement is made more compact than the arrangement linearly provided with the light sources and the collimating lenses as shown in FIGS. 14 and 15.

The plane mirror 31 of the receiving optics 20 is an oval shaped plane reflector (see FIG. 3) having a high reflectance and rotates around a rotational axis 30x coinciding with the center axis 2x of the toroidal mirror 2. Specifically, the plane mirror 31 is mounted obliquely with respect to the rotational axis 30x, and is driven rotationally around the rotational axis 30x in the directions shown by the arrows 30a in FIGS. 1 and 3 by an unillustrated driving means. The plane mirror 31 is rotated around the rotational axis 30x by about 180 degrees to cover substantially the whole area of the circular cross section 201 of the toroidal mirror 2.

Specifically, the plane mirror 31 is rotatably provided at such a position as to allow substantially all the light fluxes that have been reflected on the toroidal mirror 2 and converged on the focus point circle 2f to be incident thereon, and with such a tilt angle as to reflect the light fluxes incident onto the plane mirror 31 in the direction of the center axis 2x i.e. the rotational axis 30x. The converging position of each light flux on the focus point circle 2f is specified by the rotation angle of the plane mirror 31 so that the light flux in a specified direction is directed to an incident aperture 41a of the spectral analyzer 40.

Figure 4:
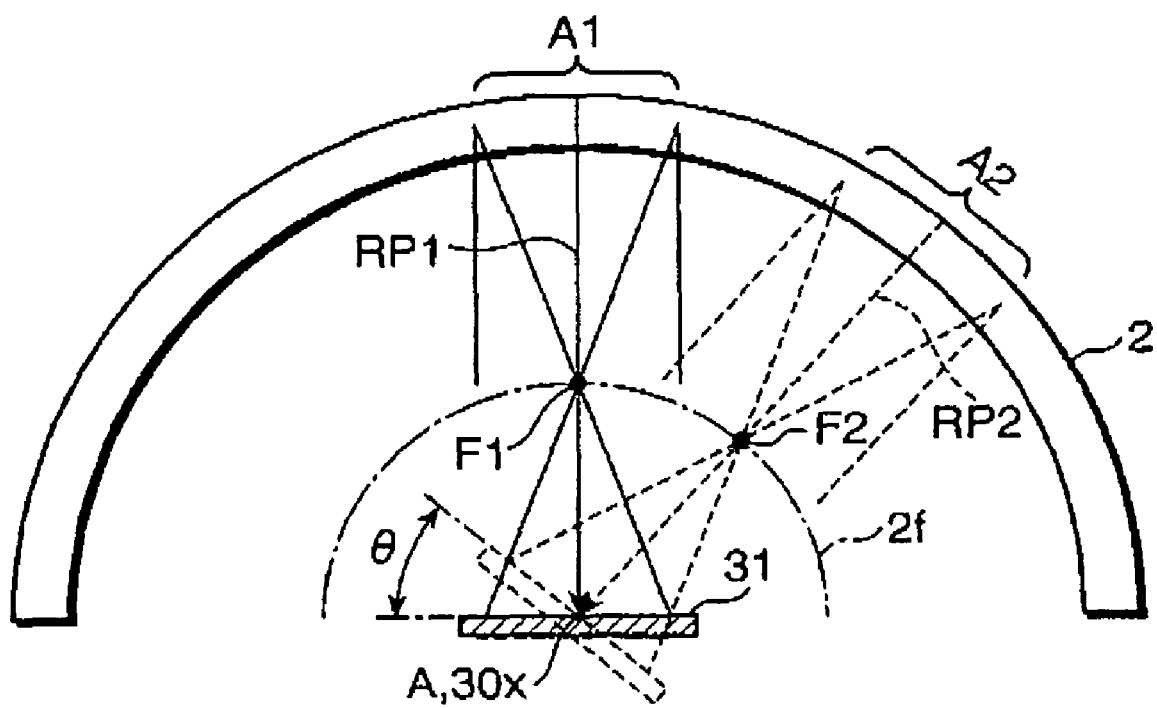
FIG. 4 is a schematic illustration showing a cross section in a perpendicular plane passing the point A in FIG. 3.

FIG. 4 is an illustration showing a function of the plane mirror 31, specifically showing a cross section in a plane passing the intersecting point "A" of a reflection surface of the plane mirror 31 shown in FIG. 3 with the center axis 2x, and perpendicular to the center axis 2x. As shown by the solid line in FIG. 4, in the case where the cross section of the plane mirror 31 is set parallel to the sample surface 1, out of the light reflected on the sample surface 1, a light flux parallel to a radius RP1 coinciding with the normal in is reflected on a reflection area A1 of the toroidal mirror 2 facing the plane mirror 31. After the reflected light flux is converged on the point F1 of the focus point circle 2f, the converged light flux is selectively converged to the incident aperture 41a.

On the other hand, as shown by the dotted line in FIG. 4, in the case where the cross section of the plane mirror 31 is rotated by a certain angle θ from the parallel position, out of the light reflected on the sample surface 1, a light flux parallel to a radius RP2, which is angularly displaced from the radius RP1 by the angle θ, is reflected on a reflection area A2 of the toroidal mirror 2 facing the plane mirror 31. After the reflected light flux is converged on the point F2 on the focus point circle 2f, the converged light flux is selectively converged to the incident aperture 41a. In this way, the plane mirror 31 serves as a selector for selectively allowing a reflected light flux to be incident to the incident aperture 41a in accordance with the rotation angle of the plane mirror 31. In other words, the optical system S1 is configured to variably set the receiving angle with respect to the illuminating direction in accordance with the rotation angle of the plane mirror 31.

The relay lens 24 comprises one or more lens elements having a positive optical power, and converges the light flux reflected along the center axis 2x by the plane mirror 31 into the incident aperture 41a. Thus, the light flux converged at the selected position on the focus point circle 2f by the rotation angle of the plane mirror 31 is re-converged into the incident aperture 41a.

The spectral analyzer 40 measures spectral intensities of the light fluxes incident into the incident aperture 41a. FIG. 5 is a schematic illustration showing an example of the spectral analyzer 40. The spectral analyzer 40 includes a collimating lens 41, a diffraction grating 42, and a photo sensor array 43.

The collimating lens 41 transmits the light flux passing through the incident aperture 41a to the diffraction grating 42 as a collimated light flux and produces a dispersed image of the incident aperture 41a on the surface of the photo sensor array 43. The diffraction grating 42 reflects and disperses the collimated light flux into the wavelength components. The photo sensor array 43 comprises a plurality of photosensitive pixels (silicon photodiodes for example) arrayed in line at even interval. The dispersed light incident in each pixel of the photo sensor array 43 is converted to a corresponding photocurrent by the photodiodes of the channel.

An analog light signal indicative of the received light component is outputted from each pixel of the photo sensor array 43, and is processed by a signal processor 501 and a calculator 502. Thus, spectral intensities of the light fluxes are obtained, as well as reflectance factors and colorimetric values based on the spectral intensities of the light fluxes. Specifically, the signal processor 501 performs amplification and digital conversion with respect to the analog light signals. The calculator 502 calculates spectral intensities, reflectance factors, and colorimetric values based on digital signals outputted from the signal processor 501.

An operation or a process of the optical system S1 having the above arrangement in the first embodiment is described. A light flux 11a emitted toward the toroidal mirror 2 from the light source 11 arranged at an anormal angle of 45 degrees with respect to the normal in is reflected on the toroidal mirror 2, and the reflected light flux is projected onto the sample surface 1 as a collimated light flux 11b with the anormal angle of 45 degrees. The collimated light flux 11b is reflected on the sample surface 1 in accordance with the reflection characteristics of the sample surface 1.

A light flux 11c which is a part of the light reflected from the sample surface 1 and is parallel to the measurement plane 2a is reflected on the toroidal mirror 2 as a reflected light flux 11d. FIGS. 1 and 2 illustrate merely the reflected light flux 11c in the direction of the normal 1n. The reflected light flux 11d is converged at a point 11e on the focus point circle 2f corresponding to the reflecting directions around the center axis 2x, because each of the parabolic cross sections 202 of the toroidal mirror 2 has a parabolic profile with a vertical line 2h as the symmetrical axis (see FIG. 2). The converging point 11e is changed depending on the reflecting direction from the toroidal mirror 2.

As mentioned above, the respective converging points 11e on the focus point circle 2f are points where images of the incident aperture 41a of the spectral analyzer 40 are produced by combined operation of the plane mirror 31 and the relay lens 24. Also, the focus point circle 2f has such a configuration that the light flux converged on the respective converging points lie of the focus point circle 2f is selected in accordance with the rotation of the plane mirror 31. With this arrangement, an optical path from the toroidal mirror 2 to the incident aperture 41a is defined in accordance with the rotation angle of the plane mirror 31. Specifically, a divergent light flux 11f out of the converging point 11e selected by the rotation of the plane mirror 31 is reflected on the plane mirror 31, and is incident along the center axis 2x or the rotational axis 30x onto the relay lens 24, which, in turn, allows the divergent light flux 11f to be incident to the incident aperture 41a, as a converged light flux 11g.

When the converged light flux 11g is incident to the incident aperture 41a, the spectral analyzer 40 measures a spectral intensity of the converged light flux 119, as a spectral intensity of the reflected light flux from the sample surface 1 in the direction defined by the rotation angle of the plane mirror 31. In the example of FIG. 1, the illumination light flux with the anormal angle of 45 degrees is projected onto the sample surface 1, and the plane mirror 31 is set at such a rotation angle as to selectively reflect the reflected light flux along the normal 1n. Accordingly, the spectral intensity of the reflected light flux with an anormal angle of 0 degree with respect to the illumination light flux is measured.

The goniometric spectrophotometer provided with the optical system S1 is particularly useful in evaluating the color of a pearlescent paint. FIGS. 6A to 6C are graphs showing reflection characteristics of a generally available solid paint, a metallic paint, and a pearlescent mica paint, wherein the illumination angle is set at −45 degrees, and the receiving angle is changed in the range of −25 degrees to 65 degrees. In the graph of FIG. 6A concerning colorimetric measurement of the solid paint, the magnitudes and the ratio of tri-stimulus values (X, Y, Z) are substantially constant except for specular reflection. This shows that the solid paint exhibits substantially the same color to any viewing direction. In the graph of FIG. 6B concerning colorimetric measurement of the metallic paint, although the magnitudes of tri-stimulus values (X, Y, Z) are varied depending on the receiving angle, the ratio of the tri-stimulus values (X, Y, Z) is stable. This means that the hue of the metallic paint appears substantially the same to any viewing direction. On the other hand, in the graph of FIG. 6C concerning colorimetric measurement of the pearlescent mica paint, not only the magnitudes of tri-stimulus values (X, Y, Z) but also the ratio thereof are changed depending on the receiving angle. This means that the hue of the pearlescent mica paint changes depending on the viewing direction.

A goniometric spectrophotometer capable of flexibly setting the receiving angle is particularly suitable for accessing the pearlescent color represented by a pearlescent paint such as the paint containing mica flakes which has the appearance highly dependent on the observing angle and require to measure the spectral intensities of light fluxes from consecutively different directions with a small interval. Further, in the goniometric spectrophotometer in the first embodiment, the observing direction is flexibly set by combined operation of the toroidal mirror 2 and the plane mirror 31 having the rotational axis 30x in agreement with the center axis 2x of the toroidal mirror 2 so as to extract a reflected light flux in any direction parallel to the measurement plane 2a out of the reflected light fluxes from the sample surface 1, whereby a spectral intensity of the extracted reflected light flux is measured by the spectral analyzer 40. Unlike the conventional goniometric spectrophotometer designed such that the entire light receiver is rotationally moved, the arrangement in the embodiment enables to produce a compact goniometric spectrophotometer because the plane mirror 31 is the only member to be rotated. Also, since the plane mirror 31 is the only member to be driven, a load to the driving means can be reduced, which enables to perform angular positioning of the plane mirror 31 within a relatively short period, thereby enabling speedy measurement.

Second Embodiment

In the following, a second embodiment as an example of a more practical goniometric spectrophotometer is described. It is desirable to solve the following drawbacks (1) to (3) of the principle optical system S1 shown in FIGS. 1 to 3 for practical application.

(1) Since the rotational axis 30x of the plane mirror 31, the optical axis of the relay lens 24, and the incident aperture 41a of the spectral analyzer 40 are in agreement with the center axis 2x of the toroidal mirror 2 substantially contacting with the sample surface 1, a part of the plane mirror 31, the relay lens 24, and the spectral analyzer 40 locate below the sample surface 1. Thus, the interference of the sample surface 1 with the part of the measuring apparatus may obstruct measurement of a large sample.

(2) After the light flux reflected on the toroidal mirror 2 is converged at the respective converging points of the focus point circle 2f. The divergent light flux is incident onto the plane mirror 31 and the relay lens 24 after the convergence. In view of this, a plane mirror and a relay optics each having a large effective diameter are required, which may increase the size and cost of the measuring apparatus.

(3) It is necessary to incorporate a reference optics for monitoring an output fluctuation of the light source 11.

Figure 7:
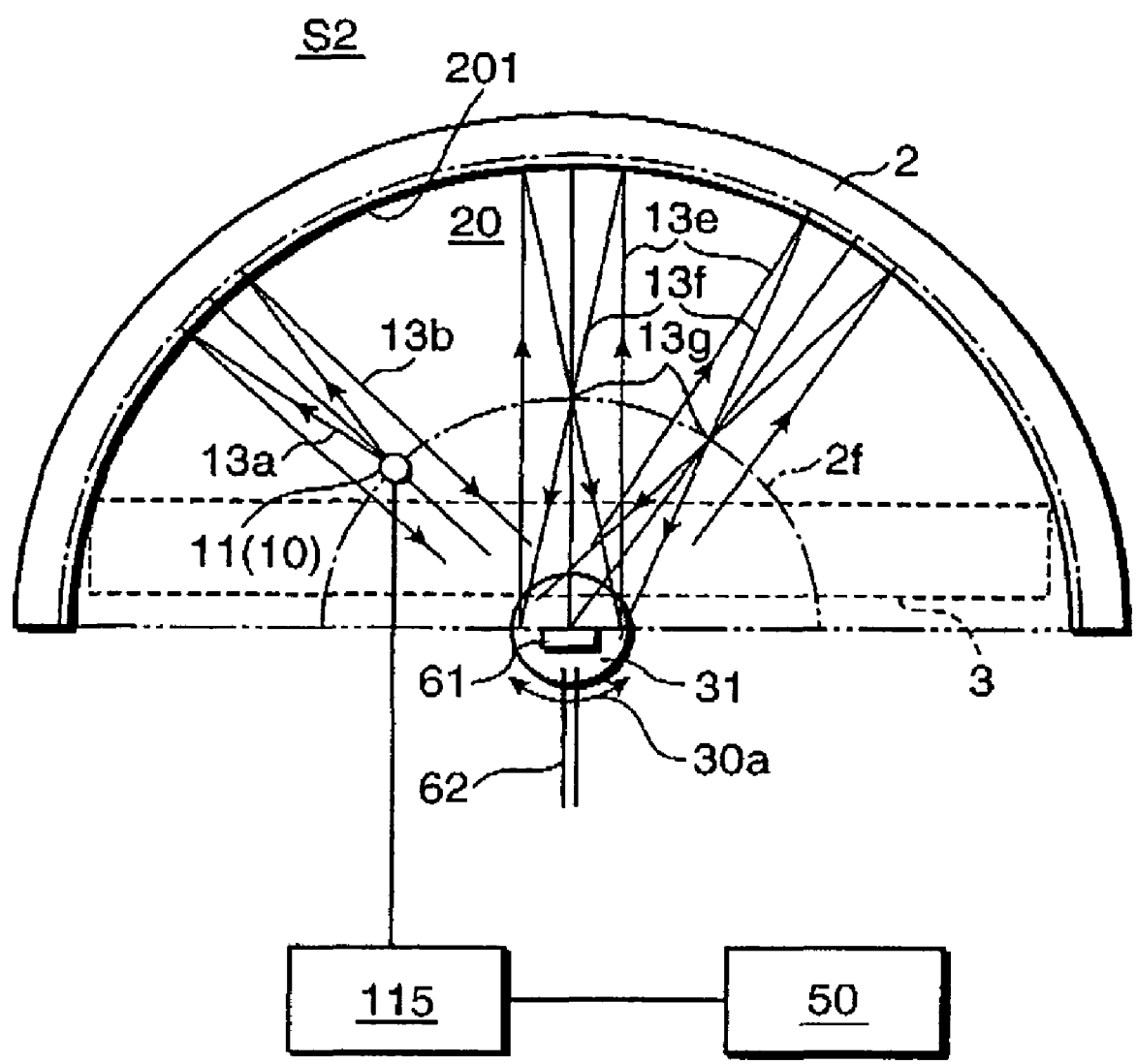
FIG. 7 is a front view showing an arrangement of an optical system in a goniometric spectrophotometer of a second embodiment of the invention.
Figure 8:
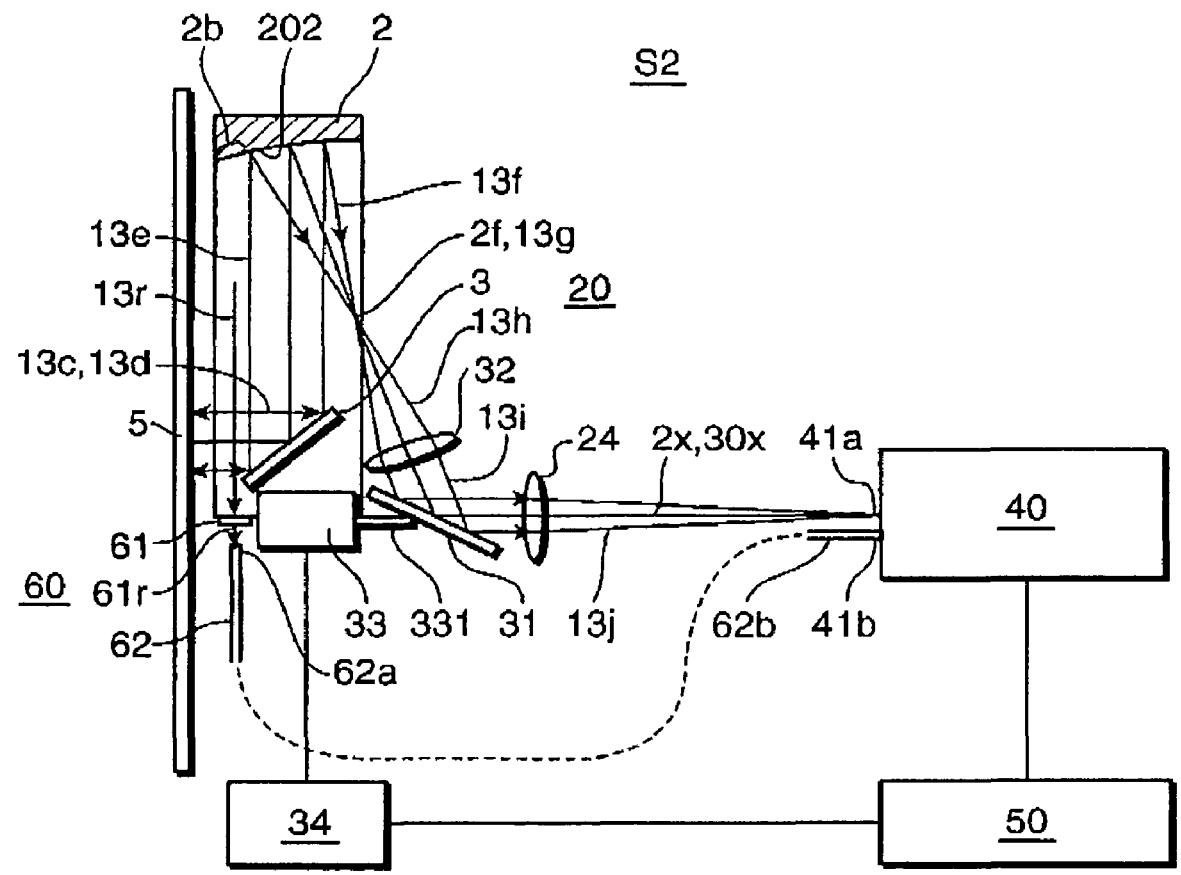
FIG. 8 is a cross-sectional side view of the optical system shown in FIG. 7 in a plane perpendicular to FIG. 7 and including a normal to a sample surface.

FIG. 7 is a front view showing an arrangement of an optical system S2 of a goniometric spectrophotometer as the second embodiment, taking into consideration of the aforementioned drawbacks (1) to (3). FIG. 8 is a cross-sectional side view of the optical system S2 in a plane perpendicular to FIG. 7 and including a normal to a surface 5 of a sample placed in a sample aperture (not shown). The optical system 52 is different from the optical system S1 in that the optical system S2 is provided with a reflective mirror 3 between a toroidal mirror 2 and the surface 5 of the sample disposed at a certain angle with respect to a center axis 2x of the toroidal mirror 2 for folding a measurement plane 2a (see FIGS. 1 and 3). With this arrangement, the aforementioned drawback (1) can be solved, and a colorimetric value of the surface 5 of a sample having a large size such as an automobile body can be measured. Also, the optical system S2 is different from the optical system S1 in that a second relay lens 32 comprising a relay optics is additionally provided between a plane mirror 31 and a focus point circle 2f, and that a reference optics 60 is provided. With these arrangements, the drawbacks (2) and (3) are solved. In the following, the second embodiment is described primarily on the differences.

The reflective mirror 3 is a plane mirror of an elongated rectangular shape, and is fixed between the center axis 2x of the toroidal mirror 2 and a reflection surface of the toroidal mirror 2 with such a tilt angle as to fold the measurement plane 2a by 90 degrees. The sample surface 5 is arranged at a position equivalent to a position substantially in contact with the center axis 2x of the toroidal mirror 2, although the optical path is folded by the reflective mirror 3. The positional relation between the toroidal mirror and the sample surface in the embodiments of the invention may include a case that the sample surface 1 is actually contacted by the center axis 2x of the toroidal mirror 2, as in the arrangement of the optical system S1, and a case that the sample surface 5 is not actually contacted but effectively contacted by the center axis 2x via the reflective mirror 3, as in the arrangement of the optical system S2.

The relay optics includes a first relay lens (first lens element) 24 provided between the plane mirror 31 and an incident aperture 41a, and the second relay lens 32 (second lens element) provided between the plane mirror 31 and the focus point circle 2f. Although the illustration of the second relay lens 32 is simplified, the second relay lens 32 is integrated with the plane mirror 31 and rotates therewith. Additionally providing the second relay lens 32 enables to suppress divergence of light fluxes converged at the respective converging points on the focus point circle 2f, thereby enabling to narrow the light fluxes onto the plane mirror 31 and the first relay lens 24. This enables to suppress the effective diameter of the plane mirror 31 and of the first relay lens 24, which contributes to realize a compact optics.

The reference optics 60 includes a diffuser 61 and a reference optical fiber 62. The reference optics 60 is arranged at such a position as to allow incidence of a reference light flux 13r, i.e. a part of a light flux that has been emitted from a light source 11 and reflected on an extension 2b extending along the center axis 2x of the toroidal mirror 2. The diffuser 61 is located on an incident plane of the reference optics 60. The diffuser 61 is an optical component having a property of diffusively transmitting a light flux incident thereon, and is provided on the center axis 2x of the toroidal mirror 2. The diffuser 61 is, as shown in FIG. 8, located at such a position that does not interfere with the reflective mirror 3. The reference optical fiber 62 has an incident end 62a on the back side of the diffuser 61 to allow a light flux 61r i.e. a part of the reference light flux 13r that has been incident onto the diffuser 61 and diffusively transmitted through the diffuser 61 to be incident into the incident end 62a as a reference light flux.

Alternatively, the incident end 62a of the reference optical fiber 62 may be directly disposed on the center axis 2x of the toroidal mirror 2 so that the reference light flux is incident to the incident end 62a of the reference optical fiber 62 without passing the diffuser 61. Allowing the reference light flux to be incident to the incident end 62a of the reference optical fiber 62 via the diffuser 61, as proposed in the embodiment, is advantageous as follows. For instance, in the case where plural light sources are arranged on the focus point circle 2f, this arrangement allows reference light fluxes originated from the light sources in the respective illuminating directions to be incident into the incident end 62a of the reference optical fiber 62, because a part of each reference light flux 13r that has been diffusively transmitted through the diffuser 61 is incident into the incident end 62a.

In the second embodiment, the spectral analyzer 40 is a dual-channel analyzer provided with two incident apertures. One of the incident apertures is an incident aperture 41a into which reflected light fluxes from the sample surface are incident via the relay optics, and the other is a reference aperture 41b into which reference light fluxes are incident. The incident aperture 41a is arranged along the center axis 2x. The reference aperture 41b is connected to an exit end 62b of the reference optical fiber 62.

An operation or a process of the optical system S2 having the above arrangement in the second embodiment is described. A light flux 13a emitted from the light source 11 arranged substantially at an anormal angle of 45 degrees is reflected on the toroidal mirror 2, and the reflected light flux is incident onto the reflective mirror 3 as a collimated light flux 13b substantially with an anormal angle of 45 degrees so that the sample surface 5 is illuminated with a collimated light flux 13c reflected on the reflective mirror 3. The collimated light flux 13c is reflected on the sample surface 5 in accordance with the reflection characteristics of the sample surface 5, as a reflected light flux 13d, which, in turn, is incident onto the reflective mirror 3 for reflection.

A part of the reflected light flux 13d parallel to the measurement plane 2a (see FIG. 3) perpendicular to the center axis 2x is reflected on the toroidal mirror 2, as a reflected light flux 13f. The reflected light flux 13f is converged at a converging point 13g of the focus point circle 2f depending on the respective reflecting directions around the center axis 2x, because each of parabolic cross sections 202 of the toroidal mirror 2 has a parabolic profile with a vertical line 2h as the symmetrical axis. The converging point 13g is selected in accordance with the rotation angle of the plane mirror 31. Thereafter, a diffused light flux 13h out of the converging point 13g selected by the rotational position of the plane mirror 31 is narrowed by the second relay lens 32. And the narrowed light flux is reflected on the plane mirror 31 along the direction of the center axis 2x for incidence onto the first relay lens 24 to be a converged light flux 13j, which in turn is incident into the incident aperture 41a.

A part of the light flux emitted from the light source 11 is reflected on the extension 2b of the toroidal mirror 2 as the reference light flux 13r so that the reference light flux 13r is projected onto the diffuser 61. A part of the reference light flux 13r that has been diffusively transmitted through the diffuser 61 is incident into the incident end 62a of the reference optical fiber 62 as a reference light flux, which in turn is transmitted to the reference aperture 41b via the reference optical fiber 62.

In the second embodiment, a stepping motor 33 and a stepping motor driver 34 are used as an example of a driving means for rotating the plane mirror 31 (see FIG. 8). An output shaft of the stepping motor 33 is directly connected to a rotary shaft 331 of the plane mirror 31. The plane mirror 31 is driven rotationally around an axis of the rotary shaft 331 when the stepping motor driver 34 outputs a predetermined number of driving pulses to the stepping motor 33. The light source 11 is controllably turned on by a light source driver 115. The light source driver 115, the stepping motor driver 34, and the spectral analyzer 40 are controlled by a control calculating unit 50.

Figure 9:
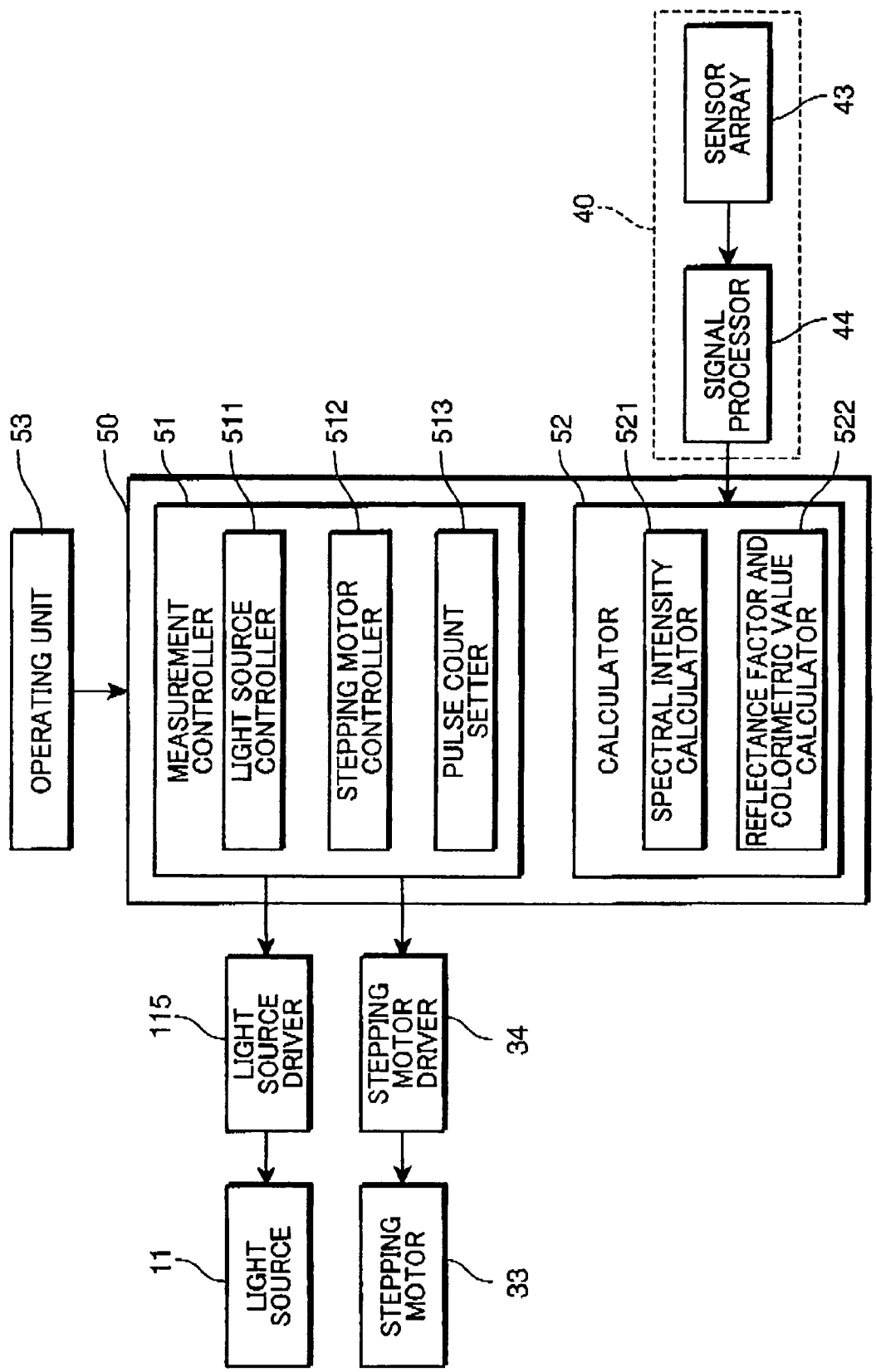
FIG. 9 is a block diagram showing functional elements of a control calculating unit in the second embodiment.

FIG. 9 is a block diagram showing functional elements of the control calculating unit 50. The control calculating unit 50 includes a central processing unit (CPU), a read only memory (ROM) storing a control program and the like, and a random access memory (RAM) for temporarily saving data for computation processing or control processing. The control calculating unit 50 functionally includes a measurement controller 51 for controlling the light source 11 and the stepping motor 33, and a calculator 52 for performing processing of a measurement signal outputted from the spectral analyzer 40. Also, the control calculating unit 50 receives an operation command signal from an operator by way of an operating unit 53.

The measurement controller 51 has a light source controller 511, a stepping motor controller 512, and a pulse count setter 513. The light source controller 511 generates a lighting control signal for controlling emission of the light source 11 in accordance with the operation command signal sent from the operating unit 53, a measurement sequence, or the like to control the emission of the light source 11 via the light source driver 115.

The stepping motor controller 512 generates a stepping motor driving signal for driving the stepping motor 33. Specifically, the stepping motor controller 512 obtains the necessary pulse count for rotating the plane mirror 31 to a predetermined angle from the pulse count setter 513, which will be described later, and supplies as many pulses as the necessary pulse count to the stepping motor driver 34 as a driving pulse signal. The stepping motor driver 34 generates a driving pulse based on the driving pulse signal, and supplies the generated driving pulse to the stepping motor 33.

The pulse count setter 513 correlates the number of pulses to a rotation angle of the plane mirror 31, and sets the pulse count data for rotating the plane mirror 31 by the predetermined angle from the initial position. When the plane mirror 31 is rotated at every 5 degree position from the initial position, for example, the pulse count data for rotating the plane mirror 31 at every 5 degree position is set for each 5 degree position. The pulse count data set by the pulse count setter 513 is read, and the read pulse count data is sent to the stepping motor controller 512 in accordance with the measurement sequence as a driving pulse signal.

The initial position of the plane mirror 31 can be the direction of specular reflection by the sample positioned at the predetermined position and illuminated by the light source 11, which is detected by the spectral analyzer 40 as the position of the maximum reflection intensity. Alternatively, the initial position of the plane mirror 31 can be detected by an additional initial position sensor such as a photo-interrupter, which is arranged at a suitable position on the plane mirror 31. However, when the sample is inclined from the right position, the measurement will be erroneous if the initial position is detected by the additional initial position sensor, unlike a case that the initial position is detected as the specular reflection by the sample.

The calculator 52 has a spectral intensity calculator 521, and a reflectance factor and colorimetric value calculator 522. The spectral intensity calculator 521 calculates a spectral intensity of a reflected light flux with respect to each of the rotation angles of the plane mirror 31 i.e. each of the predetermined receiving angles, using the spectral intensity signal which has been outputted from the sensor array 43 of the spectral analyzer 40 and processed by a signal processor 44. At the time of the calculation, a predetermined correction calculation is performed in accordance with intensity fluctuations of the reference light fluxes.

The reflectance factor and colorimetric value calculator 522 calculates a spectral reflectance factor acquired from the intensity obtained by the spectral intensity calculator 521 and converts it to colorimetric values of the sample in the respective receiving directions selected by the rotation of the plane mirror 31 by applying a predetermined color system to the spectral reflectance factors. Examples of the color system are XYZ color system, L*a*b* color system, and L*C*h* color system. Alternatively, a color difference may be obtained by applying a predetermined color difference equation to the colorimetric values. Examples of the color difference equation are L*a*b* color difference, CIE 94 color difference, and CIE 2000 color difference recommended by the International Commission on Illumination (CIE) and CMC (l:c) color difference.

Figure 10:
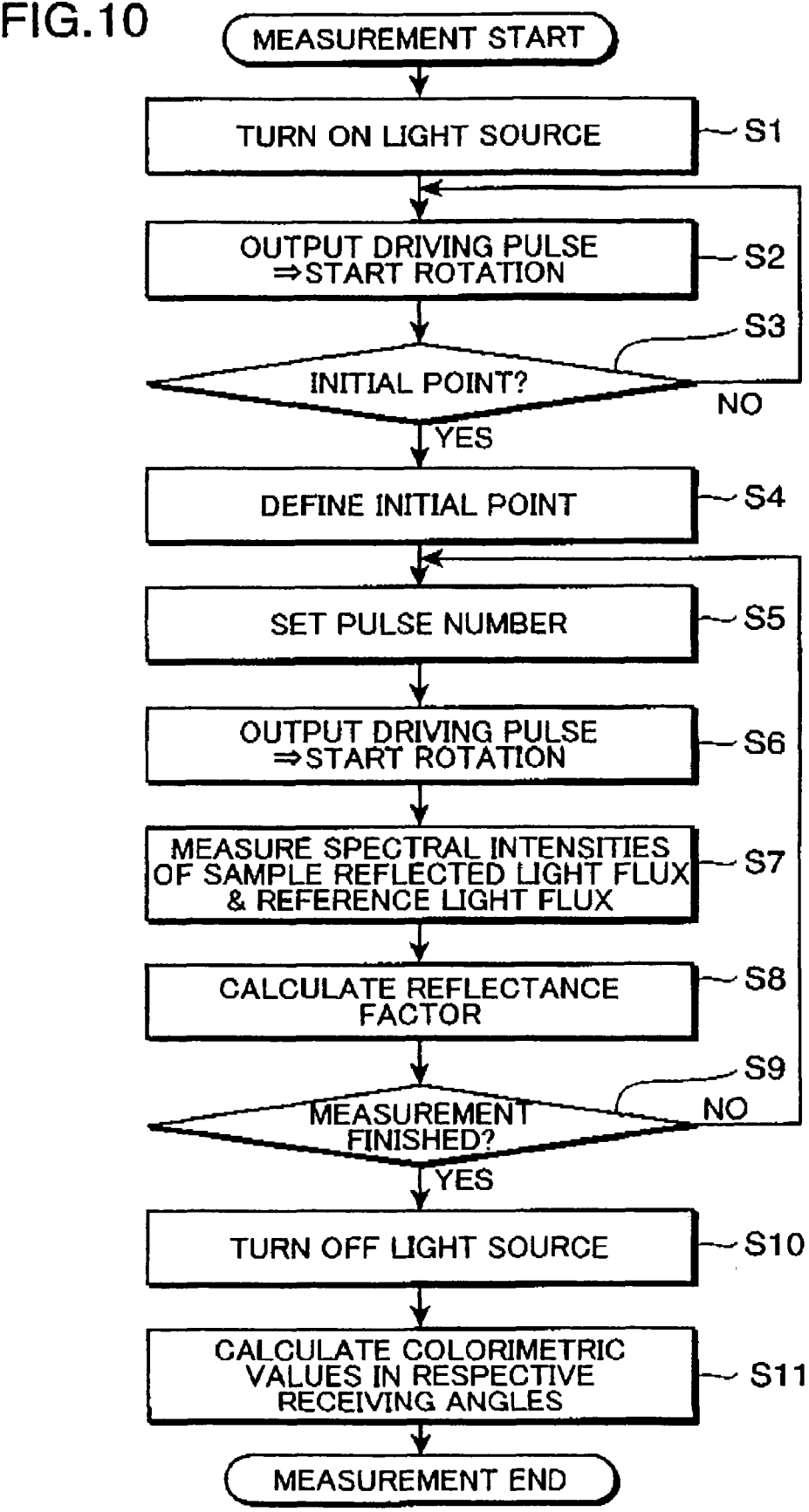
FIG. 10 is a flowchart describing operations to be executed by the goniometric spectrophotometer of the second embodiment.

An operation of the goniometric spectrophotometer in accordance with the second embodiment is described referring to a flowchart shown in FIG. 10. When a surface 5 of a sample is set in a predetermined sample aperture to start measurement, the light source 11 is turned on by the light source controller 511 (Step S1). Then, the stepping motor controller 512 sequentially generates a driving pulse for detecting specular reflection to detect the initial position of the plane mirror 31, in other words, the specular reflection position of the sample surface 5, and the stepping motor 33 is driven rotationally by every predetermined angular interval based on the driving pulse (Step S2). Thereby, the plane mirror 31 is driven rotationally around the rotary shaft 331 (see FIG. 8). At the time of the rotation of the plane mirror 31, the spectral intensity calculator 521 calculates a spectral intensity of a reflected light flux by the certain angular interval of the stepping motor 33.

Subsequently, it is judged whether the current angular position of the plane mirror 31 is the specular reflection position (Step S3). Specifically, comparison is made to judge whether the spectral intensity of the reflected light flux calculated by the spectral intensity calculator 521 reaches the maximum value. The comparison is cyclically repeated until the maximal value of the spectral intensity of the reflected light flux is detected to define the angular position of the plane mirror 31 where the spectral intensity of the reflected light flux is maximal, as the initial position of the plane mirror 31 (Step S4).

After the initial position is defined, the pulse count setter 513 sets a drive pulse number in accordance with the rotation angle of the plane mirror 31 based on the initial position (Step S5). Specifically, since the rotation angle of the stepping motor 33 can be precisely controlled by the drive pulse number, and a relation between the drive pulse number and the rotation angle can be defined in advance, the drive pulse number in accordance with the angular interval of the plane mirror 31, e.g. the drive pulse number necessary for rotating the plane mirror 31 at every 5 degree position is set. Then, the stepping motor controller 512 reads the drive pulse number for rotating the plane mirror 31 by the first rotation angle set at first in the measurement sequence, and the read drive pulse number is outputted to the stepping motor driver 34. Thereby, the stepping motor 33 rotates the plane mirror 31 by the first rotation angle (Step S6).

Then, the converged light flux at the converging point on the focus point circle $2f$ selected by the rotation angle of the plane mirror 31 is incident into the incident aperture 41a of the spectral analyzer 40, and the reference light flux incident into the incident end 62a of the reference optical fiber 62 via the diffuser 61 is incident into the reference aperture 41b. Next, the spectral intensity calculator 521 calculates the spectral intensity of the reflected light flux from the sample surface 5 and the spectral intensity of the reference light flux, as spectral intensity data (Step S7). Subsequently, the reflectance factor and colorimetric value calculator 522 calculates a spectral reflectance factor based on the spectral intensity data (Step 58). The calculated spectral reflectance factor is temporarily saved in the RAM of the control calculating unit 50.

Thereafter, it is judged whether there remains measurement to be conducted in the predetermined receiving angle (Step S9). If it is judged that there remains measurement to be conducted (NO in Step S9), the flow returns to Step S5 to cyclically repeat the measurement. For instance, the stepping motor controller 512 reads the drive pulse number for rotating the plane mirror 31 by the second rotation angle set at second in the measurement sequence. If, on the other hand, it is judged that the measurement in the predetermined receiving angle is completed (YES in Step S9), the light source 11 is turned off (Step S10). Then, the reflectance factor and colorimetric value calculator 522 calculates the colorimetric values (or color differences) in the respective receiving angles (Step 811). Thus, the processing is completed.

The above operation flow is described for the case that the stepping motor 33 is used as a driving means for rotating the plane mirror 31. In the case where the stepping motor 33 is not used, a similar measurement as mentioned above may be performed by reading rotation angle information of the plane mirror 31 detected by an initial position sensor, a position sensor, and the like.

(Description on Modified Embodiments)

(1) Modified Illumination System Incorporated with an Aperture Plate

Figure 11:
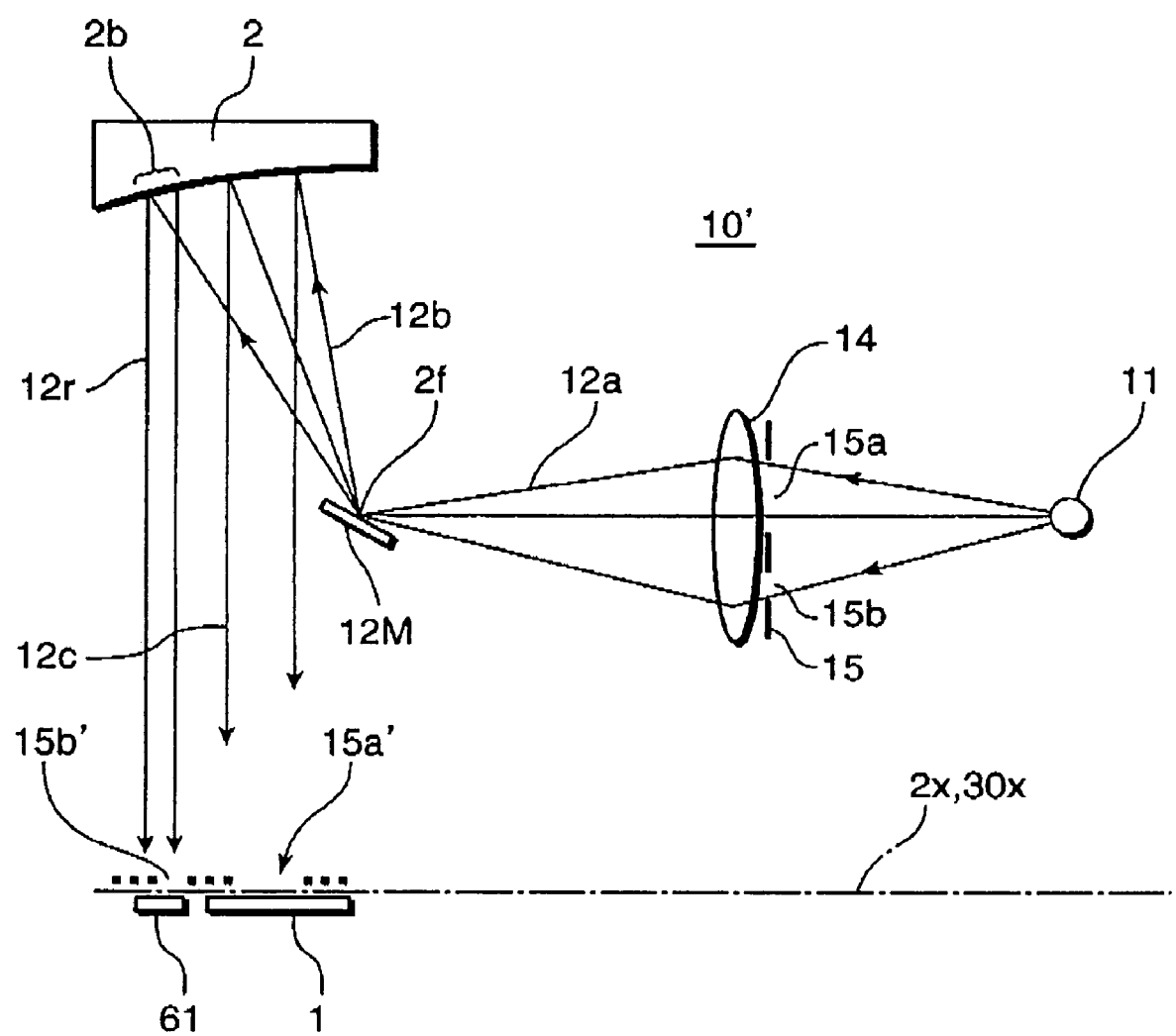
FIG. 11 is an illustration showing a variation of an illumination system.

In the first and second embodiments, the light source 11 of the illumination system 10 is arranged on the focus point circle 2f. Alternatively, an illumination system 10' as shown in FIG. 11 may be used in place of the illumination system 10. The illumination system 10' has a light source 11, a light source reflective mirror 12M, a condensing lens 14, and an aperture plate 15.

The light source reflective mirror 12M is arranged on a focus point circle 2f of a toroidal mirror 2 with a predetermined angle to reflect a light flux 12a that has been emitted from the light source 11 and converged by the condensing lens 14 so that the reflected light flux is incident onto a reflecting surface of the toroidal mirror 2 as a divergent light flux 12b. The divergent light flux 12b is collimated into a collimated light flux 12c by reflection on the toroidal mirror 2 so that the collimated light flux 12c is projected onto a sample surface 1 or a sample surface 5 via a reflective mirror 3. A part of the reflected light flux 12a that has been reflected on an extension 2b of the toroidal mirror 2 is projected onto a surface of a diffuser 61 as a reference light flux 12r.

The aperture plate 15 is provided between the light source 11 and the condensing lens 14. The aperture plate 15 is formed with a sample aperture 15a and a reference aperture 15b. The aperture plate 15 is positioned at the position equivalent to the position of the sample surface 1 to form the image on the sample surface 1 and the diffuser 61 by combined operation of the toroidal mirror 2 and the condensing lens 14. With this arrangement, a light image 15a' of the sample aperture 15a is formed on the sample surface 1, and a light image 15b' of the reference aperture 15b is formed on the surface of the diffuser 61.

In the thus constructed illumination system 10', with use of the aperture plate 15 formed with the sample aperture 15a and the reference aperture 15b, a measurement area on the sample surface 1 i.e. an illumination area on the sample surface 1 with the illumination light is confined within the area of the light image 15a' and an illumination area on the surface of the diffuser 61 with the reference light is confined within the area of the light image 15b'. This enables to suppress stray light to thereby perform more accurate colorimetric measurement.

(2) Modified Embodiment Provided with Plural Illuminators

Figure 12:
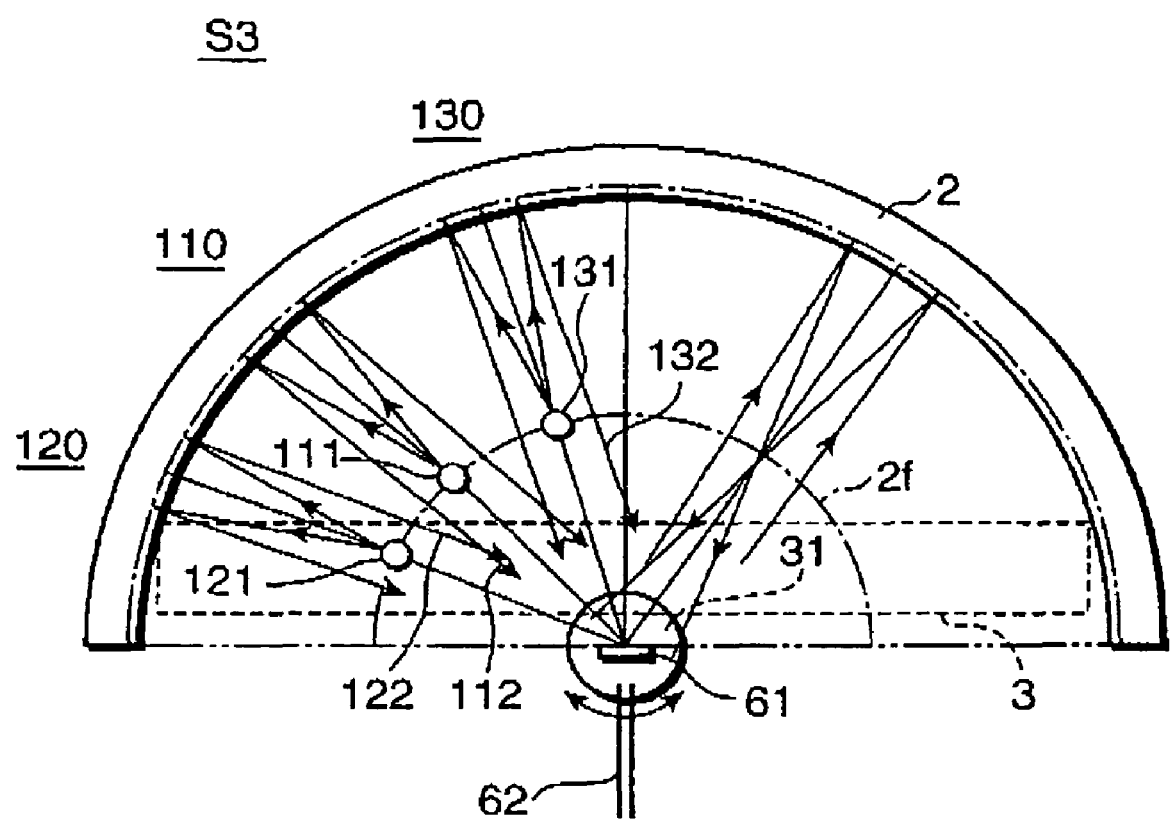
FIG. 12 is a front view showing an optical system provided with a plurality of illuminators.

In the first and second embodiments, the light source 11 of the illumination system 10 is arranged at an anormal angle of 45 degrees on the focus point circle 2f. Alternatively, a plurality of light sources may be arranged on a focus point circle 2f. FIG. 12 is a front view showing an arrangement of an optical system S3 provided with plural illuminators. The optical system S3 has a first illuminator 110 arranged at an anormal angle of 45 degrees, a second illuminator 120 arranged at an anormal angle of 65 degrees, and a third illuminator 130 arrange at an anormal angle of 15 degrees.

The first illuminator 110 has a light source 111 arranged on the focus point circle 2f with an anormal angle of 45 degrees to project a collimated light flux 112 onto a sample surface via a toroidal mirror 2. Similarly, the second illuminator 120 has a light source 121 arranged on the focus point circle 2f with an anormal angle of 65 degrees to project a collimated light flux 122 onto the sample surface via the toroidal mirror 2. Likewise, the third illuminator 130 has a light source 131 arranged on the focus point circle 2f with an anormal angle of 15 degrees to project a collimated light flux 132 onto the sample surface via the toroidal mirror 2. In this way, arranging the illuminators 110, 120, and 130 at the respective angular positions enables to speedily perform color evaluation of a pearlescent paint whose spectral reflectance factor is varied depending on an illuminating direction.

In the case of a goniometric spectrophotometer provided with the optical system S3, a control calculating unit may have a function of selectively turning on the light source 111, 121, 131 of the first, second, third illuminator 110, 120, 130, in addition to the functional elements as shown in FIG. 9. Also, a stepping motor 33 may be controllably driven in association with light emission of the light source 111, 121, 131 to drivingly rotate a plane mirror 31 so that a light flux in an intended receiving angle defined by the angular position of the plane mirror 31 is incident to an incident aperture 41a.

Further alternatively, an optical system may be configured in such a manner that a single light source is arranged on a focus point circle 2f, and the light source is made movable along the focus point circle 2f, in place of providing the first to third illuminators 110, 120, and 130. The altered optical system enables to realize an operation substantially equivalent to the operation of the optical system provided with the plural illuminators.

(3) Modified Embodiment with a Retractable Shutter at the Sample Aperture

It is desirable to provide a retractable shutter capable of openably closing a sample aperture except for a condition that a sample faces a sample aperture formed in the housing of a goniometric spectrophotometer. In the case where the retractable shutter is provided, it is desirable that the retractable shutter is driven by the power of the stepping motor 33 in the second embodiment.

Figure 13:
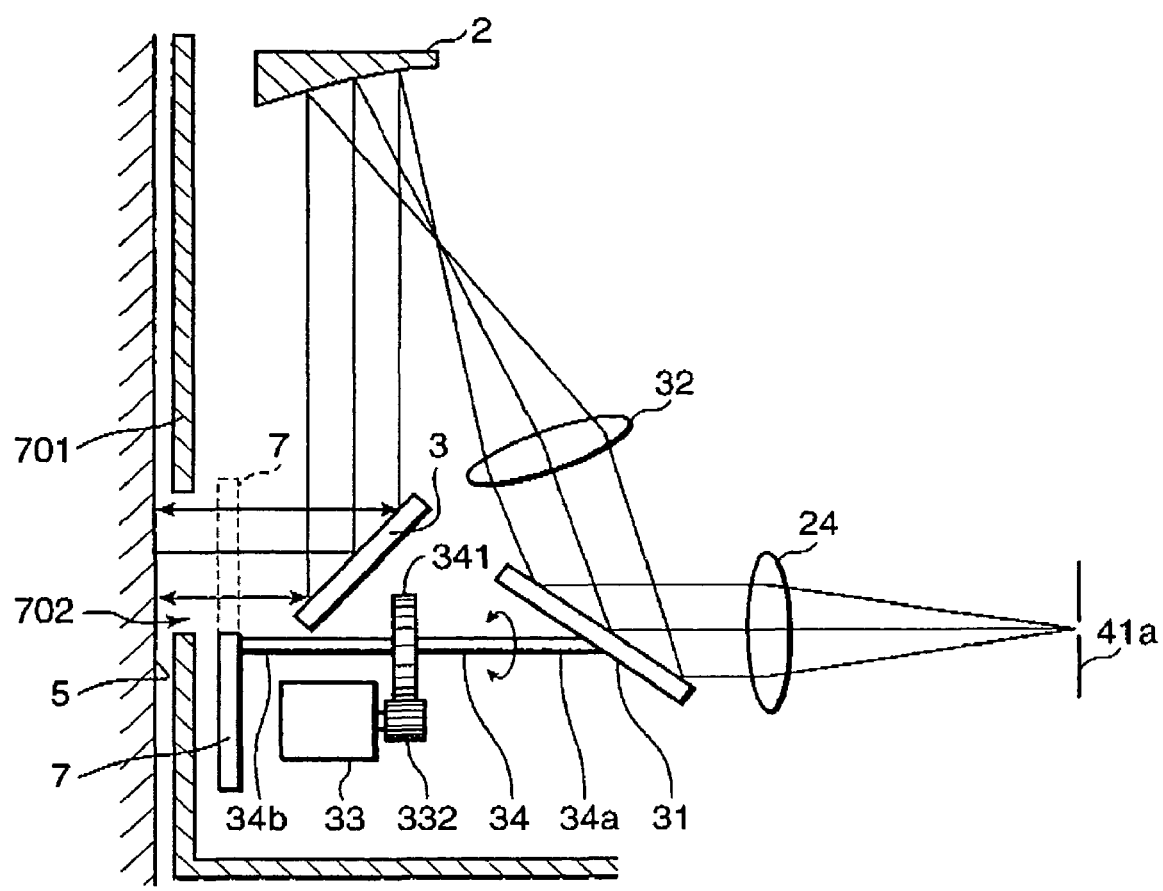
FIG. 13 is a cross-sectional side view showing a goniometric spectrophotometer provided with a retractable shutter for closing a sample aperture.

FIG. 13 is a cross-sectional side view showing essential parts of a goniometric spectrophotometer provided with a retractable shutter. As illustrated in FIG. 13, the goniometric spectrophotometer is housed in a housing 701. A sample aperture 702 is formed on the housing 701 at a position facing a sample surface 5. A gear 332 is combined to an output shaft of a stepping motor 33, and the gear 332 engages a large size gear 341 connected to a rotation shaft 34. With this arrangement, when the stepping motor 33 is driven, the rotation shaft 34 is driven rotationally in the directions shown by the arrows in FIG. 13.

The rotation shaft 34 has one end thereof fixed to a plane mirror 31, and the other end thereof fixed to an end of a plate of the retractable shutter 7 having such dimensions as to cover the sample aperture 702. Specifically, the rotation shaft 34 serves as an axis of rotation of the plane mirror 31 and as a driving axis of the retractable shutter 7. The plane mirror 31 and the retractable shutter 7 are mounted on the rotation shaft 34 with such a positional relation that the shutter 7 does not close the sample aperture 702 when the plane mirror 31 is rotated in a rotation angle range of about 180 degrees required for goniometric spectrophotometry. In other words, when the rotation shaft 34 is rotated to such an angular position that the rotation angle of the plane mirror 31 exceeds the rotation angle range of 180 degrees, the shutter 7 is moved to the position of closing the sample aperture 702, as shown by the dotted line in FIG. 13. Namely, the shutter 7 is selectively movable to a closed position where the shutter 7 closes the sample aperture 702, and a retracted position where the shutter 7 is retracted away from the sample aperture 702 to open the sample aperture 702 by the stepping motor 33 for drivingly rotating the plane mirror 31.

In the goniometric spectrophotometer provided with the shutter 7, when measurement is not performed, the sample aperture 702 can be closed by the shutter 7 by moving the shutter 7 to the closed position with use of the stepping motor 33 for rotating the plane mirror 31. This enables to protect the measuring optics and to suppress intrusion of external foreign matters such as dusts. This arrangement eliminates additional provision of a driving means for the shutter 7 or the like, thereby eliminating cost increase.

SUMMARY OF EMBODIMENTS (1) A goniometric spectrophotometer for measuring a goniometric reflection characteristic of a sample comprises: one or more illuminators; a toroidal mirror which is rotationally symmetrical with respect to a center axis substantially contacting with a surface of a sample; a light receiver including a spectral analyzer provided with an incident aperture on the center axis; a rotating optics provided with a rotation axis substantially in agreement with the center axis; and a controller for controlling operations of the illuminator, the light receiver, and the rotating optics, wherein the toroidal mirror reflects a light flux that has been emitted from the one or more illuminators and reflected on the sample surface in respective reflecting directions around the center axis and parallel to a measurement plane perpendicular to the center axis, and converges the light flux at respective converging points on a focus point circle of the toroidal mirror corresponding to the respective reflecting directions around the center axis, and wherein the light flux converged at the respective converging point on the focus point circle is selectively incident to the incident aperture of the light receiver in accordance with a rotation angle of the rotating optics around the rotation axis.

In this arrangement, arbitrarily setting the rotation angle of the rotating optics around the rotation axis by combined operation of the toroidal mirror and the rotating optics enables to extract the reflected light flux from the sample surface in a selected reflecting direction parallel to the measurement plane for measurement of a spectral intensity of the extracted light flux by the spectral analyzer. In other words, functioning the rotating optics as a selector for selecting the light flux converged at the respective converging point on the focus point circle of the toroidal mirror corresponding to the respective reflecting directions enables to extract the reflected light flux in the selected reflecting direction. This arrangement enables to make the goniometric spectrophotometer more compact, as compared with the conventional goniometric spectrophotometer designed such that the light receiver as a whole is rotationally moved, because the rotating optics with the rotation axis substantially in agreement with the center axis is the only member to be driven. Also, since measurement can be performed by merely rotating the rotating optics, a load to a driving means for rotating the rotating optics can be reduced, which enables to perform angular positioning of the rotating optics in a relatively short period.

With the goniometric spectrophotometer (1), in addition to the merit inherent to the goniometric spectrophotometer capable of flexibly measuring reflection light in an arbitrary reflecting direction merely by changing a control software controlling the rotation angle of the rotating optics or an equivalent technique, this arrangement enables to make the goniometric spectrophotometer compact and lightweight, thereby providing a portable goniometric spectrophotometer, because the rotating optics is the sole member to be driven, unlike the conventional goniometric spectrophotometer. Also, since a relatively inexpensive driver can be used and the angular positioning of the rotating optics can be performed in a relatively short period due to a reduced load to the driving means for rotating the rotating optics, this arrangement contributes to production cost reduction, and measurement time reduction.

(2) the goniometric spectrometer (1) further comprises a relay optics for converging the light flux converged at the respective converging points into the incident aperture of the light receiver, wherein the rotating optics has a plane mirror arranged obliquely relative to the rotation axis, the plane mirror being rotatable around the rotation axis by the controller, and wherein the converging point of the light flux on the focus point circle is selectively defined in accordance with a rotation angle of the plane mirror so that the light flux converged at the selected converging point is converged into the incident aperture of the light receiver by the relay optics.

In this arrangement, the light flux converged at the converging point on the focus point circle selected in accordance with the rotation angle of the plane mirror arranged obliquely relative to the rotation axis is incident into the incident aperture of the light receiver via the relay optics.

With the goniometric spectrophotometer (2), since the plane mirror is the sole member to be actually driven, a compact driving means for rotating the rotating optics can be produced, which contributes to size reduction and production cost reduction of the goniometric spectrophotometer.

(3) The relay optics, or a part of the relay optics of the goniometric spectrophotometer (2) is a fixed optics having an optical axis substantially in agreement with the center axis.

In this arrangement, since the relay optics, or the part of the relay optics is the fixed optics, the plane mirror, or the plane mirror and the part of the relay optics is the member to be actually driven. This contributes to reduction of the load to the driving means for rotating the rotating optics.

With the goniometric spectrophotometer (3), since the rotating optics is substantially constituted of the plane mirror, or the plane mirror and the part of the relay optics, the goniometric spectrometer can be realized with a simplified arrangement.

(4) The relay optics of the goniometric spectrophotometer (2) includes a first lens element having an optical axis substantially in agreement with the center axis, and a second lens element which is provided between the plane mirror and the focus point circle and is rotated with the plane mirror.

In this arrangement, since the light flux incident onto the plane mirror and the first lens element is narrowed by the second lens element, a plane mirror and a first lens element with a smaller effective diameter can be used.

With the goniometric spectrophotometer (4), since the plane mirror and the first lens element with the smaller effective diameter can be used with the help of the second lens element, a more compact and lightweight goniometric spectrophotometer can be realized.

(5) The illuminator in any one of the goniometric spectrophotometers (1) through (4) has a light source arranged substantially on the focus point circle, and the light flux emitted from the light source is collimated into a collimated light flux by reflection on the toroidal mirror for illuminating the sample surface.

In this arrangement, the collimated light flux generated with use of the toroidal mirror is projected onto the sample surface. Also, providing one or more light sources at appropriate positions on the focus point circle enables to easily change or increase the illuminating directions.

With the goniometric spectrophotometer (5), since the illuminating direction can be added or changed easily, and various geometries can be realized easily, a geometry of multi angle illumination-multi angle receiving, which is required for color evaluation of a pearlescent paint for instance, can be realized without the need of unduly cost increase.

(6) Any one of the goniometric spectrophotometers (1) through (5) further comprises a reflective mirror arranged between the toroidal mirror and the sample at a certain angle with respect to the center axis for folding the measurement plane.

In this arrangement, since the reflective mirror for folding the measurement plane is provided, the sample can be placed at such a position as to avoid an interference with the constituent elements of the goniometric spectrophotometer such as the rotating optics or the relay optics.

With the goniometric spectrometer (6), providing the reflective mirror for folding the measurement plane enables to dispose the sample at such a position as to avoid an interference with the constituent elements of the goniometric spectrophotometer. This enables to evaluate the color of a large sample such as an automobile body, for instance.

(7) In the goniometric spectrophotometer (6), the light flux which has been emitted from the light source arranged substantially on the focus point circle and reflected on the toroidal mirror is reflected on the reflective mirror to project the reflected light flux onto the sample surface, and a part of the light flux is allowed to be incident onto a reference optics arranged on the center axis without being reflected by the reflective mirror.

In this arrangement, it is possible to extract the illumination light substantially analogous to the illumination light illuminating the sample surface, as reference light.

With the goniometric spectrophotometer (7), since the illumination light substantially analogous to the illumination light illuminating the sample surface can be extracted as the reference light, precise measurement correction can be performed to compensate an output fluctuation of the illumination light or the like.

(8) The reference optics of the goniometric spectrophotometer (7) includes a diffuser arranged at an incident aperture of the reference optics on the center axis.

In this arrangement, a part of the illumination light that has diffusively transmitted through the diffuser is incident onto the reference optics. This enables to allow the reference light originated from each of plural light sources arranged on the focus point circle in respective illuminating directions to be incident onto the reference optics.

With the goniometric spectrophotometer (8), the reference light originated from each of the plural light sources arranged on the focus point circle in the respective illuminating directions is allowed to be incident onto the reference optics. This enables to simplify the construction of the reference optics.

(9) Any one of the goniometric spectrophotometers (1) through (8) has a housing formed with a sample aperture so that the sample is placed facing the sample aperture, and a retractable shutter for closing the sample aperture, the Retractable shutter being controllably movable to a closed position or a retracted position by a driving means for rotating the rotating optics.

In this arrangement, the shutter is driven by the driving means for rotating the rotating optics to close the sample aperture when measurement is not performed.

With the goniometric spectrophotometer (9), since the retractable shutter is driven by the driving means for rotating the rotating optics to close the sample aperture, this arrangement enables to suppress intrusion of external foreign matters such as dusts and protect the measuring optics. Further, this arrangement eliminates additional provision of a driving means for driving the shutter, which suppresses cost increase.

(10) An apparatus for measuring a goniometric reflection characteristic of a sample comprises: one or more illuminators; a toroidal mirror which is rotationally symmetrical with respect to a center axis substantially contacting with a surface of a sample; a light receiver provided with an incident aperture on the center axis: a rotating optics provided with a rotation axis substantially in agreement with the center axis; and a controller for controlling operations of the illuminator, the light receiver, and the rotating optics, wherein the toroidal mirror reflects a light flux that has been emitted from the one or more illuminators and reflected on the sample surface in respective reflecting directions around the center axis parallel to a measurement plane perpendicular to the center axis, and converges the light flux at respective converging points on a focus point circle of the toroidal mirror corresponding to the respective reflecting directions around the center axis, and wherein the light flux converged at the respective converging points on the focus point circle is selectively incident into the incident aperture of the light receiver in accordance with a rotation angle of the rotating optics around the rotation axis.

With the measuring apparatus (10), unlike the conventional measuring apparatus, the rotating optics is the sole member to be driven. This contributes to realize a compact and lightweight measuring apparatus, thereby providing a portable goniometric reflection characteristic measuring apparatus. Also, since the load to the driving means for rotating the rotating optics is reduced, a relatively inexpensive driving means can be used, and the angular positioning of the rotating optics can be performed in a relatively short period, which contributes to production cost reduction and measurement time reduction.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. An apparatus for measuring a goniometric reflection property of a sample comprising:
    one or more illuminators;
    a toroidal mirror which is rotationally symmetrical around a center axis effectively contacting with a surface of a sample;
    a light receiver having an incident aperture on said center axis;
    a rotating optics which rotates around a rotation axis which effectively coincides with said center axis; and
    a controller for controlling operations of said illuminators, said light receiver, and said rotating optics,
    wherein said toroidal mirror reflects light fluxes emitted from the surface of the sample illuminated by said one or more illuminators in emitting directions perpendicular to said center axis and directs each of said light fluxes to said center axis, and
    wherein said rotating optics specifies one of said light fluxes reflected by said toroidal mirror and directs said specified light flux to said incident aperture of said light receiver.

2. The apparatus according to claim 1,
    wherein said toroidal mirror converges each of said reflected light fluxes into a point on a circle of focus points of said toroidal mirror corresponding to said emitting direction of said light flux.

3. The apparatus according to claim 2, further comprising a relay optics which transmits said converged light flux to the incident aperture of said light receiver.

4. The apparatus according to claim 3,
    wherein at least a part of said relay optics is a fixed optics having an optical axis coinciding with said center axis.

5. The apparatus according to claim 4,
    wherein said rotating optics is provided with a plane mirror obliquely positioned to said rotation axis,
    said plane mirror rotates around the rotation axis; and
    wherein said relay optics comprises a first optics having an optical axis coinciding with said center axis, and a second optics location between said plane mirror and said circle of focus points and rotating together with said plane mirror.

6. The apparatus according to claim 2,
    wherein said rotating optics is provided with a plane mirror obliquely positioned to said rotation axis, and
    said plane mirror rotates around the rotation axis.

7. The apparatus according to claim 6,
    wherein the point on said circle of focus points is specified by the rotation angle of said plane mirror, and said relay optics transmits the light flux from said specified point to the incident aperture of said light receiver.

8. The apparatus according to claim 2,
    wherein each of said one or more illuminators comprises a light source effectively located on said circle of focus points, and
    said toroidal mirror reflects light emitted from said light source, and projects a collimated light flux to the sample.

9. The apparatus according to claim 2, further comprising a folding mirror, between said toroidal mirror and the sample at a predetermined angle from said center axis, for folding said light fluxes emitted from the sample.

10. The apparatus according to claim 9,
    wherein said folding mirror further folds a light flux from said light source effectively located on said circle of focus points for illuminating the sample.

11. The apparatus according to claim 2,
    wherein said light receiver comprises a spectral analyzer.

12. The apparatus according to claim 2, further comprising:
    a housing having a sample opening to which said sample faces;
    a retractable shutter for covering said sample opening; and
    a shutter driver for driving said retractable shutter,
    wherein said retractable shutter is driven by said shutter driver either to a position covering said sample opening or a position retracted therefrom.

* * * * *